United States Patent
Lam et al.

(10) Patent No.: US 9,642,916 B2
(45) Date of Patent: May 9, 2017

(54) PORPHYRIN MODIFIED TELODENDRIMERS

(71) Applicant: The Regents of the University of California, Oakland, CA (US)

(72) Inventors: Kit S. Lam, Davis, CA (US); Yuanpei Li, Davis, CA (US); Chong-Xian Pan, Sacramento, CA (US); Tzu-yin Lin, Sacramento, CA (US)

(73) Assignee: The Regents of the University of California, Oakland, CA (US)

( * ) Notice: Subject to any disclaimer, the term of this patent is extended or adjusted under 35 U.S.C. 154(b) by 150 days.

(21) Appl. No.: 13/803,878

(22) Filed: Mar. 14, 2013

(65) Prior Publication Data

US 2014/0161719 A1 Jun. 12, 2014

Related U.S. Application Data

(60) Provisional application No. 61/736,067, filed on Dec. 12, 2012.

(51) Int. Cl.
| | |
|---|---|
| A61K 47/42 | (2006.01) |
| A61K 47/48 | (2006.01) |
| A61K 49/04 | (2006.01) |
| B82Y 5/00 | (2011.01) |
| A61K 31/704 | (2006.01) |
| A61K 41/00 | (2006.01) |
| A61K 49/00 | (2006.01) |
| A61K 51/08 | (2006.01) |
| A61K 51/12 | (2006.01) |
| A61N 5/06 | (2006.01) |

(52) U.S. Cl.
CPC ...... *A61K 47/48215* (2013.01); *A61K 31/704* (2013.01); *A61K 41/0033* (2013.01); *A61K 41/0052* (2013.01); *A61K 41/0057* (2013.01); *A61K 41/0071* (2013.01); *A61K 41/0076* (2013.01); *A61K 47/488* (2013.01); *A61K 47/48015* (2013.01); *A61K 47/48069* (2013.01); *A61K 47/48123* (2013.01); *A61K 47/48253* (2013.01); *A61K 47/48815* (2013.01); *A61K 49/00* (2013.01); *A61K 49/0036* (2013.01); *A61K 49/0423* (2013.01); *A61K 51/08* (2013.01); *A61K 51/1244* (2013.01); *B82Y 5/00* (2013.01); *A61N 5/062* (2013.01)

(58) Field of Classification Search
None
See application file for complete search history.

(56) References Cited

U.S. PATENT DOCUMENTS

| | | | |
|---|---|---|---|
| 6,365,191 | B1 | 4/2002 | Burman et al. |
| 7,824,709 | B2 | 11/2010 | Ryan et al. |
| 8,895,055 | B2 | 11/2014 | Lam et al. |
| 2002/0041898 | A1 | 4/2002 | Unger et al. |
| 2003/0027863 | A1 | 2/2003 | Cruz et al. |
| 2003/0073679 | A1 | 4/2003 | Mody et al. |
| 2005/0281777 | A1* | 12/2005 | Albrecht et al. ............. 424/78.3 |
| 2006/0013885 | A1 | 1/2006 | Nah et al. |
| 2006/0127310 | A1 | 6/2006 | Russell-Jones et al. |
| 2008/0188399 | A1 | 8/2008 | Sinko et al. |
| 2009/0203706 | A1 | 8/2009 | Zhao et al. |
| 2010/0158994 | A1 | 6/2010 | Watkin |
| 2011/0286915 | A1* | 11/2011 | Lam et al. ................... 424/1.29 |
| 2012/0253191 | A1 | 10/2012 | Zheng et al. |
| 2014/0363371 | A1 | 12/2014 | Luo et al. |
| 2015/0045419 | A1 | 2/2015 | Lam et al. |
| 2016/0038605 | A1 | 2/2016 | Lam et al. |

FOREIGN PATENT DOCUMENTS

| | | |
|---|---|---|
| EP | 1230934 A | 8/2002 |
| EP | 1724295 A1 | 11/2006 |
| EP | 2007/084126 A1 | 7/2007 |
| EP | 1967212 A2 | 9/2008 |
| JP | 2001-146556 A | 5/2001 |
| WO | 99/59550 A1 | 11/1999 |
| WO | 2008/091246 A1 | 7/2008 |
| WO | 2010/039496 A1 | 4/2010 |
| WO | 2010/148346 A2 | 12/2010 |
| WO | 2012/126115 A1 | 9/2012 |
| WO | 2012/158622 A2 | 11/2012 |

(Continued)

OTHER PUBLICATIONS

Giuntini et al. (Photochem. Photobiol. Sci., 2011, 10, 759-791) Synthetic approaches for the conjugation of . . . .*
Choi et al. (Bioconjugate Chem., 1999, 10, 62-65) Poly(ethylene glycol)-block-poly(L-lysine) Dendrimer: . . . .*
Chapman et al. (J. Am. Chem. Soc. 1994, 116, 11195-11196) Hydraamphiphiles: Novel Linear Dendritic . . . .*
Chen, et al., "Fluorescence Study of Inclusion Complexes between Star-Shaped Cholic Acid Derivatives and Polycyclic Aromatic Fluorescent Probes and the Size Effects of Host and Guest Molecules," *Journal of Physical Chemistry*, vol. 112, No. 11, pp. 3402-3409 (2008).

(Continued)

*Primary Examiner* — Tigabu Kassa
(74) *Attorney, Agent, or Firm* — Kilpatrick, Townsend & Stockton LLP

(57) ABSTRACT

The present invention provides amphiphilic telodendrimers that aggregate to form nanocarriers characterized by a hydrophobic core and a hydrophilic exterior. The nanocarrier core may include amphiphilic functionality such as cholic acid or cholic acid derivatives, and the exterior may include branched or linear poly(ethylene glycol) segments. Nanocarrier cargo such as hydrophobic drugs and other materials may be sequester in the core via non-covalent means or may be covalently bound to the telodendrimer building blocks. Telodendrimer structure may be tailored to alter loading properties, interactions with materials such as biological membranes, and other characteristics.

9 Claims, 12 Drawing Sheets

(56) References Cited

FOREIGN PATENT DOCUMENTS

WO    2013/096388 A1    6/2013

OTHER PUBLICATIONS

Duncan, "Dawning Era of Polymer Therapeutics," *Nature Rev. Drug. Discov.*, vol. 2, No. 5, pp. 347-360 (2003).
Gref, et al., "Biodegradable Long-Circulating Polymeric Nanospheres," *Science American Association for the Advancement of Science*, vol. 263, No. 5153, pp. 160-1603 (1994).
Li, et al., "Antimicrobial Activities of Amine- and Guanidine-Functionalized Cholic Acid Derivatives," *Antimicrobial Agents and Chemotherapy*, vol. 43(6), pp. 1347-1349 (Jun 1999).
Li, et al., "Well-defined, reversible disulfide cross-linked micelles for on-demand paclitaxel delivery", *Biomaterials*, vol. 32, Issue 27, pp. 6633-6645 (Sep. 30, 2011).
Li, et al., "Well-Defined, Reversible Boronate Crosslinked Nanocarriers for Targeted Drug Delivery in Response to Acidic pH Values and *cis*-Diols", *Angewandte Chemie*, vol. 124, Issue 12, pp. 2918-2923 (Mar. 19, 2012).
Luo, et al., "Asymmetric Poly(ethylene glycol) Star Polymers with a Cholic Acid Core and Their Aggregation Properties," *Biomacromolecules*, vol. 10, No. 4, pp. 900-906 (2009).
Vijayalakshmi, et al., "A Simple Construction of a Bile Acid Based Dendritic Light Harvesting System," *Organic Letters*, vol. 7, No. 13, pp. 2727-2730 (2005).
Xiao, et al., "A self-assembling nanoparticle for paclitaxel delivery in ovarian cancer," *Biomaterials*, vol. 30, No. 30, pp. 6006-6016 (2009).
Xiao, et al., PEG-oligocholic acid telodendrimer micelles for the targeted delivery of doxorubicin to B-cell lymphoma, *JCR*, 155, pp. 272-281 (2011).
International Search Report and Written Opinion for PCT/US12/70508, 11 pages, mailed on Feb. 27, 2013.
International Search Report dated May 6, 2010, issued in related International Patent Application No. PCT/US2009/057852, 19 pages.
International Preliminary Report on Patentability dated Apr. 7, 2011, issued in related International Patent Application No. PCT/US2009/057852, 9 pages.
International Search Report and Written Opinion for PCT/US2012/037794, mailed Jan. 28, 2013, 10 pages.
International Search Report and Written Opinion for International Application No. PCT/US2013/074762 mailed Apr. 21, 2014.
European Application No. 12860828.8, Extended European Search Report, mailed Mar. 10, 2016, 16 pages.
European Application No. 13863207.0, Extended European Search Report, mailed Jul. 26, 2016, 7 pages.
European Search Report for European Application No. EP 12 78 6464 dated Oct. 29, 2014, 7 pages.
Gu et al., "pH-Triggered Reversible "Stealth" Polycationic Micelles," Biomacromolecules 2008, 9, 255-262.
Heffernan et al., "Disulfide-Cross linked Polyion Micelles for Delivery of Protein Therapeutics," Annals of Biomedical Engineering. vol. 37, No. 10, Oct. 2009, pp. 1993-2002.
Huh et al., "Hydrotropic polymer micelle system for delivery of paclitaxel," Journal of Controlled Release 101 (2005) 59-68.
Japanese Application No. 2011-528068, Office Action dated Dec. 25, 2013, 2 pages.
Japanese Application No. 2014-510540, Office Action mailed Jan. 5, 2016, 7 pages.
Kaminskas et al., "PEGylation of polylysine dendrimers improves absorption and lymphatic targeting following SC administration in rats," Journal of Controlled Release, 140, 2009, pp. 108-116.
Kaminskas et al., "The Impact of Molecular Weight and PEG Chain length on the Systemic Pharmacokinetics of PEGylated Poly L-lysine Dendrimers," Molecular Pharmaceutics, 2008, vol. 5, No. 3, pp. 449-463.

\* cited by examiner a)

(b)

(c)

(d)

PORPHYRIN MODIFIED TELODENDRIMERS

CROSS-REFERENCES TO RELATED APPLICATIONS

This application claims priority to U.S. Provisional Application No. 61/736,067, filed Dec. 12, 2012, which is incorporated in its entirety herein for all purposes.

STATEMENT AS TO RIGHTS TO INVENTIONS MADE UNDER FEDERALLY SPONSORED RESEARCH AND DEVELOPMENT

This invention was made with Government support under Grant No. 2R01CA115483-06, awarded by the National Institutes of Health and the National Cancer Institute, and a VA Career Development Award-2. The Government has certain rights in this invention.

BACKGROUND OF THE INVENTION

Several effective chemotherapeutic agents for treatment of various cancer types are very insoluble in water, requiring formulations that induce unwanted side effects. Recently, nanotherapeutic formulations such as Abraxane® (paclitaxel-loaded albumin nanoparticles), Doxil® (doxorubicin-loaded liposomes), and others have been shown to improve the clinical toxicity profiles of the drugs, but their anti-tumor effects are only marginally better than the original drug formulations. This has been attributed in part to the relatively large size of the nanotherapeutic formulations (generally >100 nm), which limits the extent to which the drugs can penetrate into tumor mass. In some cases, this large size also causes nanotherapeutics to be trapped in the liver and reticuloendothelial system (RES). Accordingly, there is a need to develop smaller (20-80 nm) stealth and biocompatible nanocarriers for effective delivery anti-cancer drugs in vivo.

We have recently developed several novel nanocarriers for paclitaxel (PTX) or other hydrophobic drugs. These novel nanocarriers, comprising poly(ethylene glycol) (PEG) and oligo-cholic acids, can self-assemble under aqueous conditions to form core-shell (cholane-PEG) structures that can carry PTX in the hydrophobic interior. These amphiphilic drug-loaded nanoparticles are therapeutic by themselves with improved clinical toxicity profiles. More importantly, when decorated with cancer cell surface targeting ligands and/or tumor blood vessel ligands, these nanocarriers will be able to deliver toxic therapeutic agents to the tumor sites. The final size of the nanocarriers (10 to 100 nm) is tunable by using various, or a combination of, different cholane-PEG preparations. The nanocarrier components, PEG and cholic acid, are all biocompatible and largely non-toxic. Indeed, the PTX nanotherapeutics exhibited safe profile in in vivo administration for anticancer treatment in mouse models and companion dogs. However, the nanocarriers have demonstrated some hemolytic activity both in vitro and in vivo, as well as reduced loading capacity for certain drugs. Therefore, there is a need to develop nanocarriers with improved biocompatibility and versatility.

The present invention is based on the surprising discovery that certain changes to the hydrophilic and hydrophobic segments of the constituent building blocks improve the therapeutic properties without disrupting nanocarrier assembly, addressing the needs described above.

BRIEF SUMMARY OF THE INVENTION

In some embodiments, the present invention provides a compound of formula I:

$$(B)_k\text{-}(PEG)_m\text{-}A(Y^1)_p\text{-}L^1\text{-}D\text{-}[Y^2\text{-}L^2\text{-}R]_n \quad (I)$$

wherein B can be a binding ligand; each PEG can be a polyethyleneglycol (PEG) polymer having a molecular weight of 1-100 kDa; A includes at least one branched monomer unit X and can be linked to at least one PEG group; D can be a dendritic polymer having a single focal point group, a plurality of branched monomer units X and a plurality of end groups; each $Y^1$ and $Y^2$ can be absent or a crosslinkable group that can be boronic acid, dihydroxybenzene or a thiol; each $L^1$ and $L^2$ can independently be a bond or a linker, wherein $L^1$ can be linked to the focal point group of the dendritic polymer; each R can independently be the end group of the dendritic polymer, a porphyrin, a hydrophobic group, a hydrophilic group, an amphiphilic compound or a drug, wherein at least one R group can be a porphyrin; supscript k can be 0 or 1; subscript m can be an integer from 0 to 20; subscript n can be an integer from 2 to 20, wherein subscript n can be equal to the number of end groups on the dendritic polymer; and subscript p can be from 0 to 8.

In some embodiments, the invention provides a nanocarrier having an interior and an exterior, the nanocarrier comprising a plurality of the dendrimer conjugates of the invention, wherein each compound self-assembles in an aqueous solvent to form the nanocarrier such that a hydrophobic pocket is formed in the interior of the nanocarrier, and wherein the PEG of each compound self-assembles on the exterior of the nanocarrier.

In some embodiments, the present invention provides a method of treating a disease via photodynamic or photothermal therapy, including administering to a subject in need thereof, a therapeutically effective amount of a nanocarrier of the present invention, and exposing the subject to radiation, thereby treating the disease via photodynamic or photothermal therapy.

DETAILED DESCRIPTION OF THE INVENTION

I. Definitions

Figure 1:
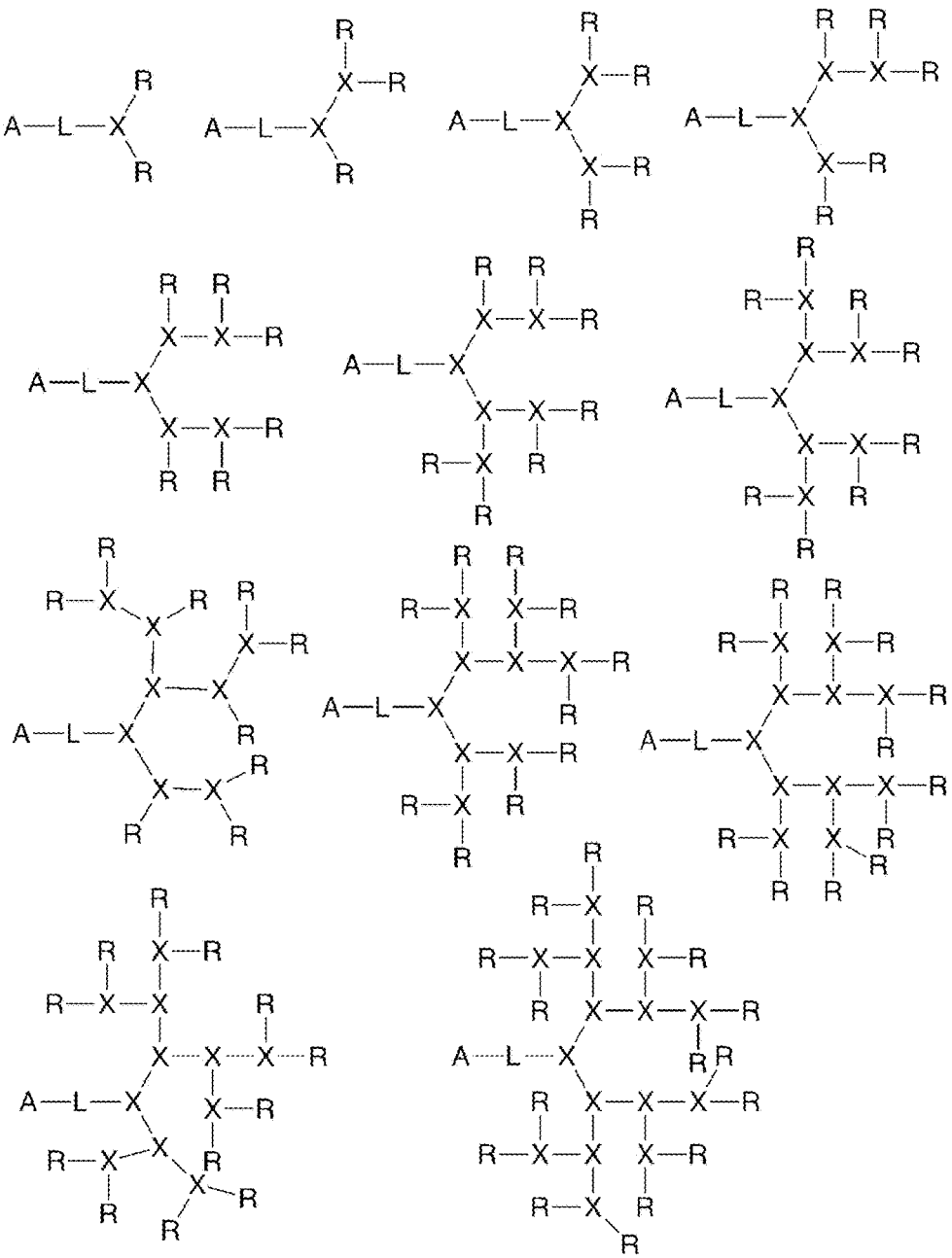
FIG. 1 shows several embodiments of the branched nature of the telodendrimers of the present invention.

As used herein, the terms "dendrimer" and "dendritic polymer" refer to branched polymers containing a focal point, a plurality of branched monomer units, and a plurality of end groups. The monomers are linked together to form arms (or "dendrons") extending from the focal point and terminating at the end groups. The focal point of the dendrimer can be attached to other segments of the compounds of the invention, and the end groups may be further functionalized with additional chemical moieties.

As used herein, the term "telodendrimer" refers to a dendrimer containing a hydrophilic PEG segment and one or more chemical moieties covalently bonded to one or more end groups of the dendrimer. These moieties can include, but are not limited to, hydrophobic groups, hydrophilic groups, amphiphilic compounds, and drugs. Different moieties may be selectively installed at a desired end groups using orthogonal protecting group strategies.

As used herein, the term "nanocarrier" refers to a micelle resulting from aggregation of the dendrimer conjugates of the invention. The nanocarrier has a hydrophobic core and a hydrophilic exterior.

As used herein, the terms "monomer" and "monomer unit" refer to a diamino carboxylic acid, a dihydroxy carboxylic acid and a hydroxyl amino carboxylic acid. Examples of diamino carboxylic acid groups of the present invention include, but are not limited to, 2,3-diamino propanoic acid, 2,4-diaminobutanoic acid, 2,5-diaminopentanoic acid (ornithine), 2,6-diaminohexanoic acid (lysine), (2-Aminoethyl)-cysteine, 3-amino-2-aminomethyl propanoic acid, 3-amino-2-aminomethyl-2-methyl propanoic acid, 4-amino-2-(2-aminoethyl) butyric acid and 5-amino-2-(3-aminopropyl) pentanoic acid. Examples of dihydroxy carboxylic acid groups of the present invention include, but are not limited to, glyceric acid, 2,4-dihydroxybutyric acid, glyceric acid, 2,4-dihydroxybutyric acid, 2,2-Bis(hydroxymethyl)propionic acid and 2,2-Bis(hydroxymethyl) butyric acid. Examples of hydroxyl amino carboxylic acids include, but are not limited to, serine and homoserine. One of skill in the art will appreciate that other monomer units are useful in the present invention.

As used herein, the term "amino acid" refers to a carboxylic acid bearing an amine functional groups. Amino acids include the diamino carboxylic acids described above. Amino acids include naturally occurring α-amino acids, wherein the amine is bound to the carbon adjacent to the carbonyl carbon of the carboxylic acid. Examples of naturally occurring α-amino acids include, but are not limited to, L-aspartic acid, L-glutamic acid, L-histidine, L-lysine, and L-arginine. Amino acids may also include the D-enantiomers of naturally occurring α-amino acids, as well as β-amino acids and other non-naturally occurring amino acids.

As used herein, the term "linker" refers to a chemical moiety that links one segment of a dendrimer conjugate to another. The types of bonds used to link the linker to the segments of the dendrimers include, but are not limited to, amides, amines, esters, carbamates, ureas, thioethers, thiocarbamates, thiocarbonate and thioureas. One of skill in the art will appreciate that other types of bonds are useful in the present invention.

As used herein, the term "oligomer" refers to five or fewer monomers, as described above, covalently linked together. The monomers may be linked together in a linear or branched fashion. The oligomer may function as a focal point for a branched segment of a telodendrimer.

As used herein, the term "hydrophobic group" refers to a chemical moiety that is water-insoluble or repelled by water. Examples of hydrophobic groups include, but are not limited to, long-chain alkanes and fatty acids, fluorocarbons, silicones, certain steroids such as cholesterol, and many polymers including, for example, polystyrene and polyisoprene.

As used herein, the term "hydrophilic group" refers to a chemical moiety that is water-soluble or attracted to water. Examples of hydrophilic groups include, but are not limited to, alcohols, short-chain carboxylic acids, quaternary amines, sulfonates, phosphates, sugars, and certain polymers such as PEG.

As used herein, the term "amphiphilic compound" refers to a compound having both hydrophobic portions and hydrophilic portions. For example, the amphiphilic compounds of the present invention can have one hydrophilic face of the compound and one hydrophobic face of the compound. Amphiphilic compounds useful in the present invention include, but are not limited to, cholic acid and cholic acid analogs and derivatives.

As used herein, the term "cholic acid" refers to (R)-4-((3R,5S,7R,8R,9S,10S,12S,13R,14S,17R)-3,7,12-trihydroxy-10,13-dimethylhexadecahydro-1H-cyclopenta[a] phenanthren-17-yl)pentanoic acid. Cholic acid is also know as 3α,7α,12α-trihydroxy-5β-cholanoic acid; 3-α, 7-α,12-α-Trihydroxy-5-β-cholan-24-oic acid; 17-β-(1-methyl-3-carboxypropyl)etiocholane-3α,7α,12α-triol; cholalic acid; and cholalin. Cholic acid derivatives and analogs, such as allocholic acid, pythocholic acid, avicholic acid, deoxycholic acid, chenodeoxycholic acid, are also useful in the present invention. Cholic acid derivatives can be designed to modulate the properties of the nanocarriers resulting from telodendrimer assembly, such as micelle stability and membrane activity. For example, the cholic acid derivatives can have hydrophilic faces that are modified with one or more glycerol groups, aminopropanediol groups, or other groups.

As used herein, the terms "drug" or "therapeutic agent" refers to an agent capable of treating and/or ameliorating a condition or disease. A drug may be a hydrophobic drug, which is any drug that repels water. Hydrophobic drugs useful in the present invention include, but are not limited to, paclitaxel, doxorubicin, etoposide, irinotecan, SN-38, cyclosporin A, podophyllotoxin, Carmustine, Amphotericin, Ixabepilone, Patupilone (epothelone class), rapamycin and platinum drugs. The drugs of the present invention also include prodrug forms. One of skill in the art will appreciate that other drugs are useful in the present invention.

As used herein, the term "crosslinkable group" or "crosslinking group" refers to a functional group capable of binding to a similar or complementary group on another molecule, for example, a first crosslinkable group on a first dendritic polymer linking to a second crosslinkable group on a second dendritic polymer. Groups suitable as crosslinkable and crosslinking groups in the present invention include thiols such as cysteine, boronic acids and 1,2-diols including 1,2-dihydroxybenzenes such as catechol. When the crosslinkable and crosslinking groups combine, they form cross-linked bonds such as disulfides and boronic esters. Other crosslinkable and crosslinking groups are suitable in the present invention.

As used herein, the term "bond cleavage component" refers to an agent capable of cleaving the cross-linked bonds formed using the crosslinkable and crosslinking groups of the present invention. The bond cleavage component can be a reducing agent, such as glutathione, when the cross-linked bond is a disulfide, or mannitol when the cross-linked bond is formed from a boronic acid and 1,2-diol.

As used herein, the term "imaging agent" refers to chemicals that allow body organs, tissue or systems to be imaged. Exemplary imaging agents include paramagnetic agents, optical probes, and radionuclides.

As used herein, the terms "treat", "treating" and "treatment" refers to any indicia of success in the treatment or amelioration of an injury, pathology, condition, or symptom (e.g., pain), including any objective or subjective parameter such as abatement; remission; diminishing of symptoms or making the symptom, injury, pathology or condition more tolerable to the patient; decreasing the frequency or duration of the symptom or condition; or, in some situations, preventing the onset of the symptom or condition. The treatment or amelioration of symptoms can be based on any objective or subjective parameter; including, e.g., the result of a physical examination.

As used herein, the term "subject" refers to animals such as mammals, including, but not limited to, primates (e.g., humans), cows, sheep, goats, horses, dogs, cats, rabbits, rats, mice and the like. In certain embodiments, the subject is a human.

As used herein, the terms "therapeutically effective amount or dose" or "therapeutically sufficient amount or dose" or "effective or sufficient amount or dose" refer to a dose that produces therapeutic effects for which it is administered. The exact dose will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins). In sensitized cells, the therapeutically effective dose can often be lower than the conventional therapeutically effective dose for non-sensitized cells.

As used herein, the term "photodynamic therapy" refers to use of nontoxic, light-sensitive compounds that become toxic to malignant or disease cells upon exposure to light. Photodynamic therapy involves a photosensitizer, a light source, and oxygen. Upon exposure to the light, the photosensitizer generates reactive oxygen species (singlet oxygen, an oxygen free radical) that react with and destroy the malignant tissue. A variety of photosensitizers can be used, including porphyrins, chlorophylls and dyes.

As used herein, the term "photothermal therapy" refers to use of nontoxic, light-sensitive compounds that generate heat upon exposure to light. Like photodynamic therapy, photothermal therapy involves a photosensitizer and a source of light, typically infrared. But photothermal therapy does not require oxygen. A variety of photosensitizers can be used, including porphyrins, chlorophylls and dyes.

II. Telodendrimers

The invention provides amphiphilic telodendrimer conjugates having a hydrophilic poly(ethylene glycol) (PEG) segment and a hydrophobic segment, and at least one porphyrin. The PEG segment can have a branched or linear architecture including one or more PEG chains. The hydrophobic segment of the telodendrimer can be provided by cholic acid, which has a hydrophobic face and a hydrophilic face. The porphyrin, cholic acid and the PEG are connected by oligomers and/or polymers that can contain a variety of acid repeats units. Typically, the oligomers and polymers comprise a diamino carboxylic acid, lysine. The telodendrimers can aggregate in solution to form micelles with a hydrophobic interior and a hydrophilic exterior. The micelles can be used as nanocarriers to deliver drugs or other agents having low water solubility.

In some embodiments, the present invention provides conjugates having a polyethylene glycol (PEG) polymer; at least two amphiphilic compounds having both a hydrophilic face and a hydrophobic face; at least one porphyrin; optionally at least two crosslinking groups; and a dendritic polymer covalently attached to the PEG, the amphiphilic compounds, the porphyrin and the crosslinking groups, wherein each conjugate self-assembles in an aqueous solvent to form the nanocarrier such that a hydrophobic pocket is formed in the interior of the nanocarrier by the orientation of the hydrophobic face of each amphiphilic compound towards each other, wherein the PEG of each conjugate self-assembles on the exterior of the nanocarrier.

In some embodiments, the present invention provides a compound of formula I:

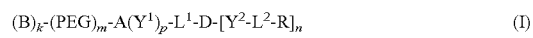

$$(B)_k\text{-}(PEG)_m\text{-}A(Y^1)_p\text{-}L^1\text{-}D\text{-}[Y^2\text{-}L^2\text{-}R]_n \qquad (I)$$

wherein B can be a binding ligand; each PEG can be a polyethyleneglycol (PEG) polymer having a molecular weight of 1-100 kDa; A includes at least one branched monomer unit X and can be linked to at least one PEG group; D can be a dendritic polymer having a single focal point group, a plurality of branched monomer units X and a plurality of end groups; each $Y^1$ and $Y^2$ can be absent or a crosslinkable group that can be boronic acid, dihydroxybenzene or a thiol; each $L^1$ and $L^2$ can independently be a bond or a linker, wherein $L^1$ can be linked to the focal point group of the dendritic polymer; each R can independently be the end group of the dendritic polymer, a porphyrin, a hydrophobic group, a hydrophilic group, an amphiphilic compound or a drug, wherein at least one R group can be a porphyrin; supscript k can be 0 or 1; subscript m can be an integer from 0 to 20; subscript n can be an integer from 2 to 20, wherein subscript n can be equal to the number of end groups on the dendritic polymer; and subscript p can be from 0 to 8.

Any suitable binding ligand can be used in the compounds of the present invention. For example, the binding ligand can target a particular organ, healthy tissue or disease tissue. Exemplary binding ligands include the PLZ4 ligand, having the amino acid sequence QDGRMGF. See U.S. application Ser. No. 13/497,041, filed Sep. 23, 2010, now U.S. Publication No. 2012/0230994.

The linkers $L^1$ and $L^2$ can include any suitable linker. In general, the linkers are bifunctional linkers, having two functional groups for reaction with each of two telodendrimer segments. In some embodiments, the linkers $L^1$ and $L^2$ can be a heterobifunctional linker. In some embodiments, the linkers $L^1$ and $L^2$ can be a homobifunctional linker. In some embodiments, the linkers $L^1$ and $L^2$ can independently be polyethylene glycol, polyserine, polyglycine, poly(serine-glycine), aliphatic amino acids, 6-amino hexanoic acid, 5-amino pentanoic acid, 4-amino butanoic acid or beta-alanine One of skill in the art will recognize that the size and chemical nature of the linker can be varied based on the structures of the telodendrimer segments to be linked.

In some embodiments, linkers $L^1$ and $L^2$ can have the formula:

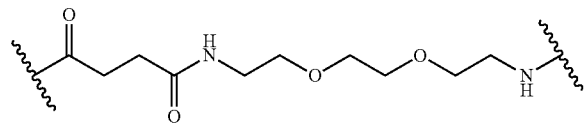 [SMILES: *NCCOCCOCCNC(=O)CCC(*)=O]

Polyethylene glycol (PEG) polymers of any size and architecture are useful in the nanocarriers of the present invention. In some embodiments, the PEG is from 1-100 kDa. In other embodiments, the PEG is from 1-10 kDa. In some other embodiments, the PEG is about 3 kDa. In still other embodiments, additional PEG polymers are linked to the amphiphilic compounds. For example, when the amphiphilic compound is cholic acid, up to 3 PEG polymers are linked to each cholic acid. The PEG polymers linked to the amphiphilic compounds are from 200-10,000 Da in size. In yet other embodiments, the PEG polymers linked to the amphiphilic compounds are from 1-5 kDa in size. One of skill in the art will appreciate that other PEG polymers and other hydrophilic polymers are useful in the present invention. PEG can be any suitable length.

The dendritic polymer can be any suitable dendritic polymer. The dendritic polymer can be made of branched monomer units including amino acids or other bifunctional AB2-type monomers, where A and B are two different functional groups capable of reacting together such that the resulting polymer chain has a branch point where an A-B bond is formed. In some embodiments, each branched monomer unit X can be a diamino carboxylic acid, a dihydroxy carboxylic acid and a hydroxyl amino carboxylic acid. In some embodiments, each diamino carboxylic acid can be 2,3-diamino propanoic acid, 2,4-diaminobutanoic acid, 2,5-diaminopentanoic acid (ornithine), 2,6-diaminohexanoic acid (lysine), (2-Aminoethyl)-cysteine, 3-amino-2-aminomethyl propanoic acid, 3-amino-2-aminomethyl-2-methyl propanoic acid, 4-amino-2-(2-aminoethyl) butyric acid or 5-amino-2-(3-aminopropyl) pentanoic acid. In some embodiments, each dihydroxy carboxylic acid can be glyceric acid, 2,4-dihydroxybutyric acid, 2,2-Bis(hydroxymethyl)propionic acid, 2,2-Bis(hydroxymethyl)butyric acid, serine or threonine. In some embodiments, each hydroxyl amino carboxylic acid can be serine or homoserine. In some embodiments, the diamino carboxylic acid is an amino acid. In some embodiments, each branched monomer unit X is lysine.

The dendritic polymer of the telodendrimer can be any suitable generation of dendrimer, including generation 1, 2, 3, 4, 5, or more, where each "generation" of dendrimer refers to the number of branch points encountered between the focal point and the end group following one branch of the dendrimer. The dendritic polymer of the telodendrimer can also include partial-generations such as 1.5, 2.5, 3.5, 4.5, 5.5, etc., where a branch point of the dendrimer has only a single branch. See, for example, the structures in FIG. 1. The various architectures of the dendritic polymer can provide any suitable number of end groups, including, but not limited to, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31 or 32 end groups.

The focal point of a telodendrimer or a telodendrimer segment can be any suitable functional group. In some embodiments, the focal point includes a functional group that allows for attachment of the telodendrimer or telodendrimer segment to another segment. The focal point functional group can be a nucleophilic group including, but not limited to, an alcohol, an amine, a thiol, or a hydrazine. The focal point functional group may also be an electrophile such as an aldehyde, a carboxylic acid, or a carboxylic acid derivative including an acid chloride or an N-hydroxysuccinimidyl ester.

The R groups installed at the telodendrimer periphery can be any suitable chemical moiety, including porphyrins, hydrophilic groups, hydrophobic groups, or amphiphilic compounds, wherein at least one R group can be a porphyrin. Any suitable porphyrin can be used in the telodendrimers of the present invention. Representative porphyrins suitable in the present invention include, but are not limited to, pyropheophorbide-a, pheophorbide, chlorin e6, purpurin or purpurinimide. In some embodiments, the porphyrin can be pyropheophorbide-a. Representative structures are shown below:

| PORPHYRIN | STRUCTURE |
|---|---|
| Porphyrin | 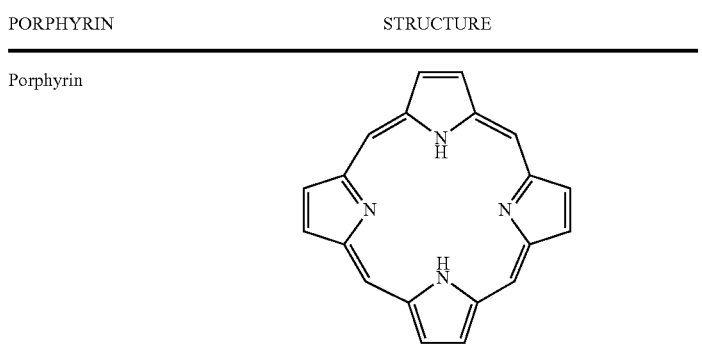 |

-continued
| PORPHYRIN | STRUCTURE |
|---|---|
| Pyropheophorbide-a | 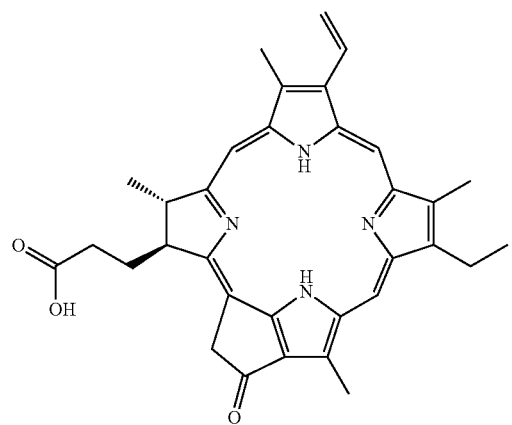 [SMILES: C=Cc1c(C)c2cc3nc(c4c5[nH]c(cc6nc(cc1[nH]2)C(C)=C6CC)c(C)c5C(=O)C4)[C@@H](CCC(=O)O)[C@@H]3C] |
| Pheophorbide | 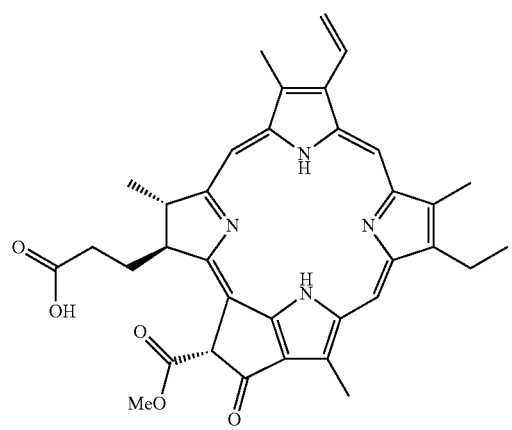 [SMILES: C=Cc1c(C)c2cc3nc(c4c5[nH]c(cc6nc(cc1[nH]2)C(C)=C6CC)c(C)c5C(=O)[C@@H]4C(=O)OC)[C@@H](CCC(=O)O)[C@@H]3C] |
| Chlorin e6 | 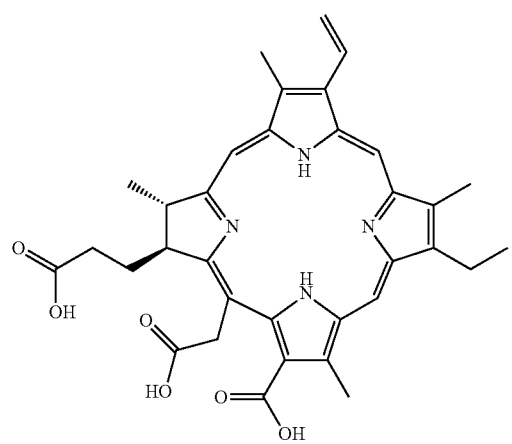 [SMILES: C=Cc1c(C)c2cc3nc(c(CC(=O)O)c4[nH]c(cc5nc(cc1[nH]2)C(C)=C5CC)c(C)c4C(=O)O)[C@@H](CCC(=O)O)[C@@H]3C] |

| PORPHYRIN | STRUCTURE |
|---|---|
| Purpurin | 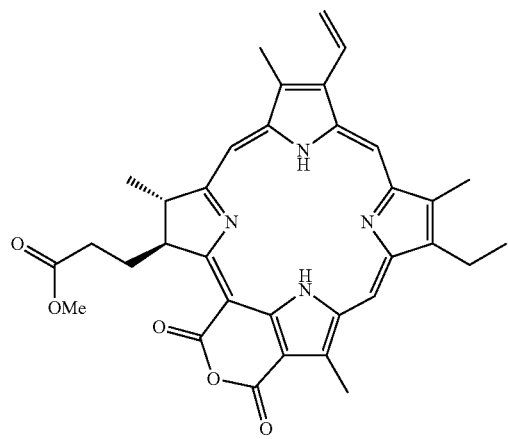 [SMILES: C=Cc1c(C)c2cc3nc(c4c5[nH]c(cc6nc(cc1[nH]2)C(C)=C6CC)c(C)c5C(=O)OC4=O)[C@@H](CCC(=O)OC)[C@@H]3C] |
| Purpurinimide | 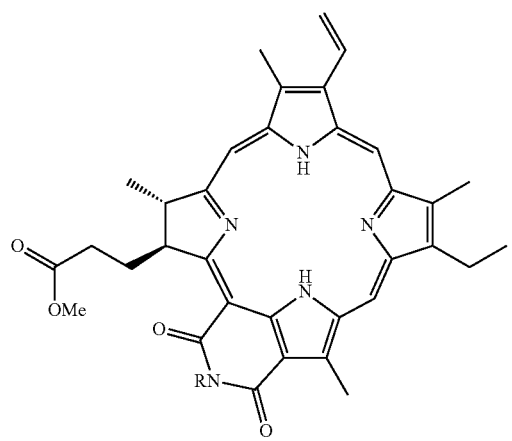 |

Examples of hydrophobic groups include, but are not limited to, long-chain alkanes and fatty acids, fluorocarbons, silicones, certain steroids such as cholesterol, and many polymers including, for example, polystyrene and polyisoprene. Examples of hydrophilic groups include, but are not limited to, alcohols, short-chain carboxylic acids, amines, sulfonates, phosphates, sugars, and certain polymers such as PEG. Examples of amphiphilic compounds include, but are not limited to, molecules that have one hydrophilic face and one hydrophobic face.

Amphiphilic compounds useful in the present invention include, but are not limited to, cholic acid and cholic acid analogs and derivatives. "Cholic acid" refers to (R)-4-((3R,5S,7R,8R,9S,10S,12S,13R,14S,17R)-3,7,12-trihydroxy-10,13-dimethylhexadecahydro-1H-cyclopenta[a]phenanthren-17-yl)pentanoic acid, having the structure:

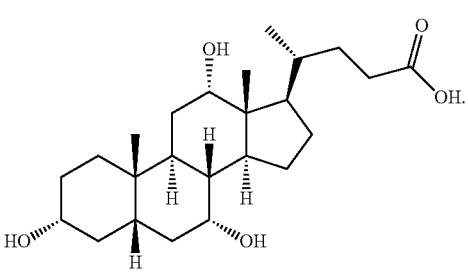

Cholic acid derivatives and analogs include, but are not limited to, allocholic acid, pythocholic acid, avicholic acid, deoxycholic acid, and chenodeoxycholic acid. Cholic acid derivatives can be designed to modulate the properties of the nanocarriers resulting from telodendrimer assembly, such as micelle stability and membrane activity. For example, the cholic acid derivatives can have hydrophilic faces that are modified with one or more glycerol groups, aminopropanediol groups, or other groups.

Telodendrimer end groups may also include drugs such as paclitaxel, doxorubicin, etoposide, irinotecan, SN-38, cyclosporin A, podophyllotoxin, carmustine, amphotericin, ixabepilone, patupilone (epothelone class), rapamycin and platinum drugs. One of skill in the art will appreciate that other drugs are useful in the present invention.

In some embodiments, each remaining R can be cholic acid, (3α, 5β, 7α, 12α)-7,12-dihydroxy-3-(2,3-dihydroxy-1-propoxy)-cholic acid, (3α, 5β, 7α, 12α)-7-hydroxy-3,12-di(2,3-dihydroxy-1-propoxy)-cholic acid, (3α, 5β, 7α, 12α)-7,12-dihydroxy-3-(3-amino-2-hydroxy-1-propoxy)-cholic acid, cholesterol formate, doxorubicin, or rhein. In other embodiments, each remaining R can be cholic acid.

The telodendrimer backbone can vary, depending on the number of branches and the number and chemical nature of the end groups and R groups, which will modulate solution conformation, rheological properties, and other characteristics. The telodendrimers can have any suitable number n of end groups and any suitable number of R groups. In some embodiments, n can be 2-70, or 2-50, or 2-30, or 2-10. In some embodiment, n is 2-20.

The telodendrimer can have a single type of R group on the periphery, or any combination of R groups in any suitable ratio. In general, at least half the number n of R groups are other than an end group. For example, at least half the number n of R groups can be a hydrophobic group, a hydrophilic group, an amphiphilic compound, a drug, or any combination thereof. In some embodiments, half the number n of R groups are amphiphilic compounds.

In some embodiments, the compound has the structure:

wherein each R can independently be a porphyrin, an amphiphilic compound or a drug, wherein at least one R group is a porphyrin.

In some embodiments, the compound has the structure:

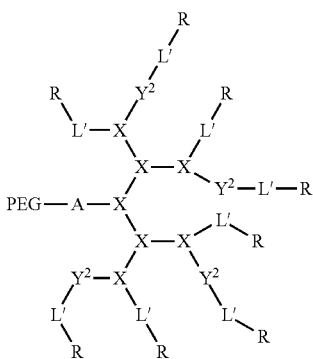

wherein PEG can be PEG5k, each branched monomer unit X can be lysine, A can be lysine, each $L^2$ can be a bond or linker Ebes, each $Y^2$ can be absent or can be cysteine; and each R can be a cholic acid or a porphyrin.

In some embodiments, the compound has the structure:

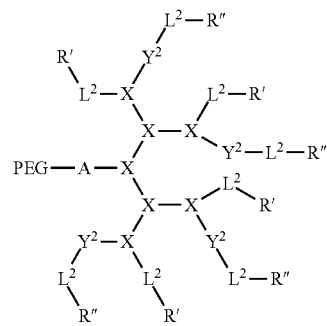

wherein each R' can be cholic acid (CA), (3α, 5β, 7α, 12α)-7,12-dihydroxy-3-(2,3-dihydroxy-1-propoxy)-cholic acid (CA-4OH), (3α, 5β, 7α, 12α)-7-hydroxy-3,12-di(2,3-dihydroxy-1-propoxy)-cholic acid (CA-5OH) or (3α, 5β, 7α, 12α)-7,12-dihydroxy-3-(3-amino-2-hydroxy-1-propoxy)-cholic acid (CA-3OH—NH$_2$); and each R" can be a porphyrin selected from the group consisting of pyropheophorbide-a, pheophorbide, chlorin e6, purpurin and purpurinimide. In other embodiments, the porphyrin can be pyropheophorbide-a. In some other embodiments, subscript k is 1. In some other embodiments, the compound can be:

(1) each $L^2$ is a bond, each $Y^2$ is absent, each R' is cholic acid, each R" is pyropheophorbide-a, and subscript k is 0;
(2) each $L^2$ is the linker Ebes, each $Y^2$ is absent, each R' is cholic acid, each R" is pyropheophorbide-a, and subscript k is 0;
(3) each $L^2$ is a bond, each $Y^2$ is cysteine, each R' is cholic acid, each R" is pyropheophorbide-a, and subscript k is 0;
(4) each $L^2$ is the linker Ebes, each $Y^2$ is cysteine, each R' is cholic acid, each R" is pyropheophorbide-a, and subscript k is 0;
(5) each $L^2$ is a bond, each $Y^2$ is absent, each R' is cholic acid, each R" is pyropheophorbide-a, and subscript k is 1;
(6) each $L^2$ is the linker Ebes, each $Y^2$ is absent, each R' is cholic acid, each R" is pyropheophorbide-a, and subscript k is 1;
(7) each $L^2$ is a bond, each $Y^2$ is cysteine, each R' is cholic acid, each R" is pyropheophorbide-a, and subscript k is 1; or
(8) each $L^2$ is the linker Ebes, each $Y^2$ is cysteine, each R' is cholic acid, each R" is pyropheophorbide-a, and subscript k is 1.

In some embodiments, the compound has the structure:

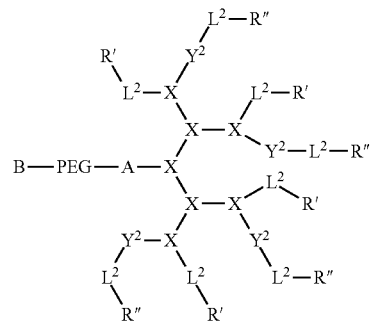

wherein each R' can be cholic acid (CA), (3α, 5β, 7α, 12α)-7,12-dihydroxy-3-(2,3-dihydroxy-1-propoxy)-cholic acid (CA-4OH), (3α, 5β, 7α, 12α)-7-hydroxy-3,12-di(2,3-dihydroxy-1-propoxy)-cholic acid (CA-5OH) or (3α, 5β, 7α, 12α)-7,12-dihydroxy-3-(3-amino-2-hydroxy-1-propoxy)-cholic acid (CA-3OH—NH$_2$); and each R" can be a porphyrin selected from the group consisting of pyropheophorbide-a, pheophorbide, chlorin e6, purpurin and purpurinimide. In other embodiments, the porphyrin can be pyropheophorbide-a. In some other embodiments, subscript k is 1. In some other embodiments, the compound can be:

| Compound | B | PEG (mw) | A | X | L$^2$ | Y$^2$ | R' | R" |
|---|---|---|---|---|---|---|---|---|
| 1 | absent | 5k | lysine | lysine | bond | absent | cholic acid | pyropheophorbide-a |
| 2 | absent | 5k | lysine | lysine | Ebes | absent | cholic acid | pyropheophorbide-a |
| 3 | absent | 5k | lysine | lysine | bond | cysteine | cholic acid | pyropheophorbide-a |
| 4 | absent | 5k | lysine | lysine | Ebes | cysteine | cholic acid | pyropheophorbide-a |
| 5 | PLZ4 | 5k | lysine | lysine | bond | absent | cholic acid | pyropheophorbide-a |
| 6 | PLZ4 | 5k | lysine | lysine | Ebes | absent | cholic acid | pyropheophorbide-a |
| 7 | PLZ4 | 5k | lysine | lysine | bond | cysteine | cholic acid | pyropheophorbide-a |
| 8 | PLZ4 | 5k | lysine | lysine | Ebes | cysteine | cholic acid | pyropheophorbide-a |

The compounds of the present invention can also include a metal cation chelated to the porphyrin. Any suitable metal can be chelated by the porphyrin. Metals useful in the present invention include the alkali metals, alkali earth metals, transition metals and post-transition metals. Alkali metals include Li, Na, K, Rb and Cs. Alkaline earth metals include Be, Mg, Ca, Sr and Ba. Transition metals include Sc, Ti, V, Cr, Mn, Fe, Co, Ni, Cu, Zn, Y, Zr, Nb, Mo, Tc, Ru, Rh, Pd, Ag, Cd, La, Hf, Ta, W, Re, Os, Ir, Pt, Au, Hg and Ac. Post-transition metals include Al, Ga, In, Tl, Ge, Sn, Pb, Sb, Bi, and Po. Radionuclides of any of these metals can also be chelated by the porphyrins. In some embodiments, the a metal cation can be chelated to the porphyrin. In other embodiments, the metal cation can be a radio-metal cation. In some other embodiments, the radio-metal cation chelated to the porphyrin can be $^{64}$Cu, $^{67}$Cu, $^{177}$Lu, $^{67}$Ga, $^{111}$In, and $^{90}$Yt.

III. Telodendrimers with Branched PEG Moieties

The telodendrimers of the present invention contain two branched segments that are linked together at their focal points. Generally, the telodendrimers include any telodendrimer as described above or as described previously (WO 2010/039496) and branched PEG segment containing two or more PEG chains bound to an oligomer focal point.

The dendritic polymer of the telodendrimer can be any suitable generation of dendrimer, including generation 1, 2, 3, 4, 5, or more, where each "generation" of dendrimer refers to the number of branch points encountered between the focal point and the end group following one branch of the dendrimer. The dendritic polymer of the telodendrimer can also include partial-generations such as 1.5, 2.5, 3.5, 4.5, 5.5, etc., where a branch point of the dendrimer has only a single branch. See, for example, the structures in FIG. 1. The various architectures of the dendritic polymer can provide any suitable number of end groups, including, but not limited to, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31 or 32 end groups.

In some embodiments, the compound can be:

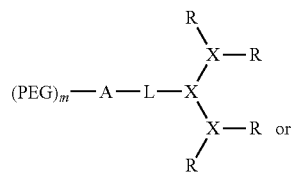

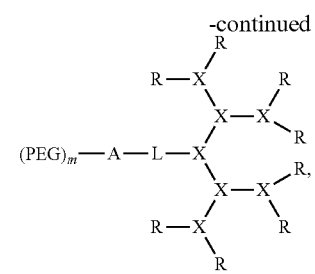

wherein each branched monomer unit X is lysine.

In some embodiments, the compound can be:

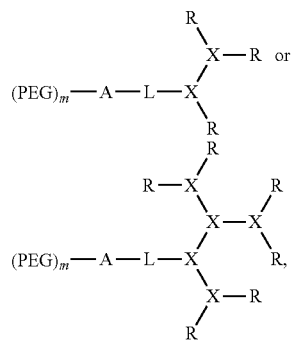

wherein each branched monomer unit X is lysine.

The PEG-oligomer unit in the telodendrimers may contain any suitable number of PEG moieties. PEG moieties may be installed site-selectively at various positions on the oligomer using orthogonal protecting groups. In some embodiments, the (PEG)$_m$-A portion of the compound can be:

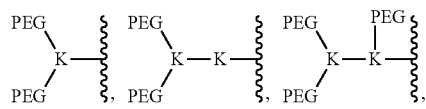

-continued

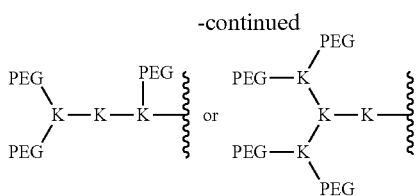

wherein each K is lysine.

In some embodiments, the telodendrimer can be:

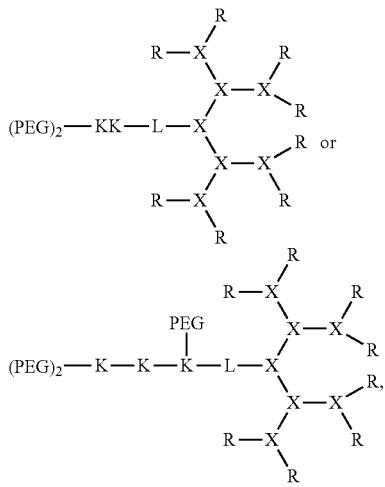

wherein each K is lysine; each PEG is PEG2k; each branched monomer unit X is lysine; each R is cholic acid; and linker L has the formula:

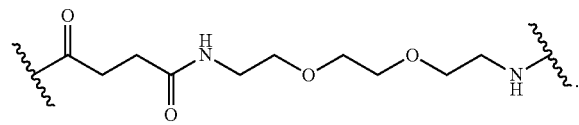

IV. Nanocarriers

The telodendrimers of the present invention aggregate to form nanocarriers with a hydrophobic core and a hydrophilic exterior. In some embodiments, the invention provides a nanocarrier having an interior and an exterior, the nanocarrier comprising a plurality of the dendrimer conjugates of the invention, wherein each compound self-assembles in an aqueous solvent to form the nanocarrier such that a hydrophobic pocket is formed in the interior of the nanocarrier, and wherein the PEG of each compound self-assembles on the exterior of the nanocarrier.

In some embodiments, each conjugate of the nanocarrier have a polyethylene glycol (PEG) polymer; at least two amphiphilic compounds having both a hydrophilic face and a hydrophobic face; at least one porphyrin; optionally at least two crosslinking groups; and a dendritic polymer covalently attached to the PEG, the amphiphilic compounds, the porphyrin and the crosslinking groups, wherein each conjugate self-assembles in an aqueous solvent to form the nanocarrier such that a hydrophobic pocket is formed in the interior of the nanocarrier by the orientation of the hydrophobic face of each amphiphilic compound towards each other, wherein the PEG of each conjugate self-assembles on the exterior of the nanocarrier. In other embodiments, each conjugate is a compound of formula I.

In some embodiments, the nanocarrier includes a hydrophobic drug or an imaging agent, such that the hydrophobic drug or imaging agent is sequestered in the hydrophobic pocket of the nanocarrier. Hydrophobic drugs useful in the nanocarrier of the present invention includes any drug having low water solubility. In some embodiments, the hydrophobic drug in the nanocarrier can be bortezomib, paclitaxel, SN38, camptothecin, etoposide and doxorubicin, docetaxel, daunorubicin, VP16, prednisone, dexamethasone, vincristine, vinblastine, temsirolimus and carmusine.

In some embodiments, the nanocarrier includes at least one monomer unit that is optionally linked to an optical probe, a radionuclide, a paramagnetic agent, a metal chelate or a drug. The drug can be a variety of hydrophilic or hydrophobic drugs, and is not limited to the hydrophobic drugs that are sequestered in the interior of the nanocarriers of the present invention.

Drugs that can be sequestered in the nanocarriers or linked to the conjugates of the present invention include, but are not limited to, cytostatic agents, cytotoxic agents (such as for example, but not limited to, DNA interactive agents (such as cisplatin or doxorubicin)); taxanes (e.g. taxotere, taxol); topoisomerase II inhibitors (such as etoposide); topoisomerase I inhibitors (such as irinotecan (or CPT-11), camptostar, or topotecan); tubulin interacting agents (such as paclitaxel, docetaxel or the epothilones); hormonal agents (such as tamoxifen); thymidilate synthase inhibitors (such as 5-fluorouracil); anti-metabolites (such as methotrexate); alkylating agents (such as temozolomide (TEMODAR™ from Schering-Plough Corporation, Kenilworth, N.J.), cyclophosphamide); aromatase combinations; ara-C, adriamycin, cytoxan, and gemcitabine. Other drugs useful in the nanocarrier of the present invention include but are not limited to Uracil mustard, Chlormethine, Ifosfamide, Melphalan, Chlorambucil, Pipobroman, Triethylenemelamine, Triethylenethiophosphoramine, Busulfan, Carmustine, Lomustine, Streptozocin, Dacarbazine, Floxuridine, Cytarabine, 6-Mercaptopurine, 6-Thioguanine, Fludarabine phosphate, oxaliplatin, leucovirin, oxaliplatin (ELOXATIN™ from Sanofi-Synthelabo Pharmaceuticals, France), Pentostatine, Vinblastine, Vincristine, Vindesine, Bleomycin, Dactinomycin, Daunorubicin, Doxorubicin, Epirubicin, Idarubicin, Mithramycin, Deoxycoformycin, Mitomycin-C, L-Asparaginase, Teniposide 17.alpha.-Ethinylestradiol, Diethylstilbestrol, Testosterone, Prednisone, Fluoxymesterone, Dromostanolone propionate, Testolactone, Megestrolacetate, Methylprednisolone, Methyltestosterone, Prednisolone, Triamcinolone, Chlorotrianisene, Hydroxyprogesterone, Aminoglutethimide, Estramustine, Medroxyprogesteroneacetate, Leuprolide, Flutamide, Toremifene, goserelin, Cisplatin, Carboplatin, Hydroxyurea, Amsacrine, Procarbazine, Mitotane, Mitoxantrone, Levamisole, Navelbene, Anastrazole, Letrazole, Capecitabine, Reloxafine, Droloxafine, or Hexamethylmelamine. Prodrug forms are also useful in the present invention.

Other drugs useful in the present invention also include radionuclides, such as $^{67}$Cu, $^{90}$Y, $^{123}$I, $^{125}$I, $^{131}$I, $^{177}$Lu, $^{188}$Re, $^{186}$Re and $^{211}$At. In some embodiments, a radionuclide can act therapeutically as a drug and as an imaging agent.

Imaging agents include paramagnetic agents, optical probes and radionuclides. Paramagnetic agents include iron particles, such as iron nanoparticles that are sequestered in the hydrophobic pocket of the nanocarrier.

In some embodiments, the conjugates can be crosslinked via the crosslinking groups. The crosslinking groups can be any suitable crosslinking group, as described above. In some embodiments, the crosslinking groups can be thiol, boronic acid or dihydroxybenzene. In some embodiments, the crosslinking groups can be thiol. In some embodiments, a first set of conjugates includes boronic acid crosslinking groups, and a second set of conjugates includes dihydroxybenzene crosslinking groups. In some embodiments, each conjugate of the nanocarrier includes at least two cholic acids, at least two pryopheophorbide-a groups, and at least two crosslinking groups, wherein the conjugates of the nanocarrier are crosslinked via the crosslinking groups.

The nanocarriers can include any suitable porphrying, as described above. In some embodiments, the porphyrin can be pyrpheophorbide-a. In some embodiments, the porphyrin groups can be chelated to a metal, as described above. Any suitable metal can be chelated to the porphyrins, including radioactive and non-radioactive metals, as described above. In some embodiments, the nanocarriers include a metal chelated to at least one of the pyropheophorbide-a groups.

Some embodiments of the invention provide nanocarriers wherein each amphiphilic compound R is independently cholic acid, allocholic acid, pythocholic acid, avicholic acid, deoxycholic acid, or chenodeoxycholic acid.

The nanocarriers of the present invention can also include a binding ligand for binding to a target moiety. The binding ligand can be linked to one of the conjugates of the nanocarrier, or can be separate. Any suitable binding ligand can be used in the compounds of the present invention, as described above. For example, the binding ligand can target a particular organ, healthy tissue or disease tissue. Exemplary binding ligands include the PLZ4 ligand, having the amino acid sequence QDGRMGF. In some embodiments, the nanocarrier including at least one binding conjugate including a polyethylene glycol (PEG) polymer, a binding ligand linked to the PEG polymer, at least two amphiphilic compounds having both a hydrophilic face and a hydrophobic face, a dendritic polymer covalently attached to the PEG and the amphiphilic compounds, wherein each binding conjugate self-assembles with the first conjugates in an aqueous solvent to form the nanocarrier such that a hydrophobic pocket is formed in the interior of the nanocarrier by the orientation of the hydrophobic face of each amphiphilic compound towards each other, wherein the PEG of each conjugate self-assembles on the exterior of the nanocarrier.

V. Method of Treating

The nanocarriers of the present invention can be used to treat any disease requiring the administration of a drug, such as by sequestering a hydrophobic drug in the interior of the nanocarrier, or by covalent attachment of a drug to a conjugate of the nanocarrier. The nanocarriers can also be used for imaging, by sequestering an imaging agent in the interior of the nanocarrier, or by attaching the imaging agent to a conjugate of the nanocarrier.

In some embodiments, the present invention provides a method of treating a disease, including administering to a subject in need of such treatment, a therapeutically effective amount of a nanocarrier of the present invention, wherein the nanocarrier includes a drug. The drug can be a covalently attached to a conjugate of the nanocarrier. In some embodiments, the drug is a hydrophobic drug sequestered in the interior of the nanocarrier. In some embodiments, the nanocarrier also includes an imaging agent. The imaging agent can be a covalently attached to a conjugate of the nanocarrier, or the imaging agent can be sequestered in the interior of the nanocarrier. In some other embodiments, both a hydrophobic drug and an imaging agent are sequestered in the interior of the nanocarrier. In still other embodiments, both a drug and an imaging agent are covalently linked to a conjugate or conjugates of the nanocarrier. In yet other embodiments, the nanocarrier can also include a radionuclide.

The methods of treating using the nanocarriers of the present invention also includes treating a disease by photodynamic therapy or photothermal therapy. The methods generally involve administering a nanocarrier of the present invention to a subject, and then exposing the subject to radiation of a specific wavelength to induce the photodynamic or photothermal therapy depending on the wavelength of light. Upon exposure to the radiation or light, the porphyrins used in the nanocarriers of the present invention, either complexed to a metal or not, generate either the reactive singlet oxygen suitable for photodynamic therapy, or generate heat sufficient of photothermal therapy. In some embodiments, the present invention provides a method of treating a disease via photodynamic or photothermal therapy, including administering to a subject in need thereof, a therapeutically effective amount of a nanocarrier of the present invention, and exposing the subject to radiation, thereby treating the disease via photodynamic or photothermal therapy. In some embodiments, the method is a method of treating a disease via photodynamic therapy. In other embodiments, the method is a method of treating a disease via photothermal therapy.

In other embodiments, the present invention provides a method of treating a disease via sonodynamic therapy, including administering to a subject in need thereof, a therapeutically effective amount of a nanocarrier of the present invention, and exposing the subject to a sonic wave, thereby treating the disease via sonodynamic therapy.

The nanocarriers of the present invention can be administered to a subject for treatment, e.g., of hyperproliferative disorders including cancer such as, but not limited to: carcinomas, gliomas, mesotheliomas, melanomas, lymphomas, leukemias, adenocarcinomas, breast cancer, ovarian cancer, cervical cancer, glioblastoma, leukemia, lymphoma, prostate cancer, and Burkitt's lymphoma, head and neck cancer, colon cancer, colorectal cancer, non-small cell lung cancer, small cell lung cancer, cancer of the esophagus, stomach cancer, pancreatic cancer, hepatobiliary cancer, cancer of the gallbladder, cancer of the small intestine, rectal cancer, kidney cancer, bladder cancer, prostate cancer, penile cancer, urethral cancer, testicular cancer, cervical cancer, vaginal cancer, uterine cancer, ovarian cancer, thyroid cancer, parathyroid cancer, adrenal cancer, pancreatic endocrine cancer, carcinoid cancer, bone cancer, skin cancer, retinoblastomas, multiple myelomas, Hodgkin's lymphoma, and non-Hodgkin's lymphoma (see, CANCER: PRINCIPLES AND PRACTICE (DeVita, V. T. et al. eds 2008) for additional cancers).

Other diseases that can be treated by the nanocarriers of the present invention include: (I) inflammatory or allergic diseases such as systemic anaphylaxis or hypersensitivity responses, drug allergies, insect sting allergies; inflammatory bowel diseases, such as Crohn's disease, ulcerative colitis, ileitis and enteritis; vaginitis; psoriasis and inflammatory dermatoses such as dermatitis, eczema, atopic dermatitis, allergic contact dermatitis, urticaria; vasculitis; spondyloarthropathies; scleroderma; respiratory allergic diseases such as asthma, allergic rhinitis, hypersensitivity lung diseases, and the like, (2) autoimmune diseases, such as arthritis (rheumatoid and psoriatic), osteoarthritis, multiple sclerosis, systemic lupus erythematosus, diabetes mellitus, glomerulonephritis, and the like, (3) graft rejection (including allograft rejection and graft-v-host disease), and (4) other diseases in which undesired inflammatory responses are to be inhibited (e.g., atherosclerosis, myositis, neurological conditions such as stroke and closed-head injuries, neurodegenerative diseases, Alzheimer's disease, encephalitis, meningitis, osteoporosis, gout, hepatitis, nephritis, sepsis, sarcoidosis, conjunctivitis, otitis, chronic obstructive pulmonary disease, sinusitis and Behcet's syndrome). In some embodiments, the disease can be cancer. In other embodiments, the disease can be bladder cancer or ovarian cancer.

In addition, the nanocarriers of the present invention are useful for the treatment of infection by pathogens such as viruses, bacteria, fungi, and parasites. Other diseases can be treated using the nanocarriers of the present invention.

Any suitable conjugate or nanocarrier can be used in the methods of the present invention. In some embodiments, each conjugate of the nanocarrier includes at least two cholic acids, at least two pryopheophorbide-a groups, at least two crosslinking groups, and a metal chelated to at least one of the pyropheophorbide-a groups, wherein the conjugates of the nanocarrier are crosslinked via the crosslinking groups.

A. Formulations

The nanocarriers of the present invention can be formulated in a variety of different manners known to one of skill in the art. Pharmaceutically acceptable carriers are determined in part by the particular composition being administered, as well as by the particular method used to administer the composition. Accordingly, there are a wide variety of suitable formulations of pharmaceutical compositions of the present invention (see, e.g., *Remington's Pharmaceutical Sciences*, 20$^{th}$ ed., 2003, supra). Effective formulations include oral and nasal formulations, formulations for parenteral administration, and compositions formulated for with extended release.

Formulations suitable for oral administration can consist of (a) liquid solutions, such as an effective amount of a compound of the present invention suspended in diluents, such as water, saline or PEG 400; (b) capsules, sachets, depots or tablets, each containing a predetermined amount of the active ingredient, as liquids, solids, granules or gelatin; (c) suspensions in an appropriate liquid; (d) suitable emulsions; and (e) patches. The liquid solutions described above can be sterile solutions. The pharmaceutical forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, e.g., sucrose, as well as pastilles comprising the active ingredient in an inert base, such as gelatin and glycerin or sucrose and acacia emulsions, gels, and the like containing, in addition to the active ingredient, carriers known in the art.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form. The composition can, if desired, also contain other compatible therapeutic agents. Preferred pharmaceutical preparations can deliver the compounds of the invention in a sustained release formulation.

Pharmaceutical preparations useful in the present invention also include extended-release formulations. In some embodiments, extended-release formulations useful in the present invention are described in U.S. Pat. No. 6,699,508, which can be prepared according to U.S. Pat. No. 7,125,567, both patents incorporated herein by reference.

The pharmaceutical preparations are typically delivered to a mammal, including humans and non-human mammals. Non-human mammals treated using the present methods include domesticated animals (i.e., canine, feline, murine, rodentia, and lagomorpha) and agricultural animals (bovine, equine, ovine, porcine).

In practicing the methods of the present invention, the pharmaceutical compositions can be used alone, or in combination with other therapeutic or diagnostic agents.

B. Administration

The nanocarriers of the present invention can be administered as frequently as necessary, including hourly, daily, weekly or monthly. The compounds utilized in the pharmaceutical method of the invention are administered at the initial dosage of about 0.0001 mg/kg to about 1000 mg/kg daily. A daily dose range of about 0.01 mg/kg to about 500 mg/kg, or about 0.1 mg/kg to about 200 mg/kg, or about 1 mg/kg to about 100 mg/kg, or about 10 mg/kg to about 50 mg/kg, can be used. The dosages, however, may be varied depending upon the requirements of the patient, the severity of the condition being treated, and the compound being employed. For example, dosages can be empirically determined considering the type and stage of disease diagnosed in a particular patient. The dose administered to a patient, in the context of the present invention should be sufficient to effect a beneficial therapeutic response in the patient over time. The size of the dose also will be determined by the existence, nature, and extent of any adverse side-effects that accompany the administration of a particular compound in a particular patient. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. For convenience, the total daily dosage may be divided and administered in portions during the day, if desired. Doses can be given daily, or on alternate days, as determined by the treating physician. Doses can also be given on a regular or continuous basis over longer periods of time (weeks, months or years), such as through the use of a subdermal capsule, sachet or depot, or via a patch or pump.

The pharmaceutical compositions can be administered to the patient in a variety of ways, including topically, parenterally, intravenously, intradermally, subcutaneously, intramuscularly, colonically, rectally or intraperitoneally. Preferably, the pharmaceutical compositions are administered parenterally, topically, intravenously, intramuscularly, subcutaneously, orally, or nasally, such as via inhalation.

In practicing the methods of the present invention, the pharmaceutical compositions can be used alone, or in combination with other therapeutic or diagnostic agents. The additional drugs used in the combination protocols of the present invention can be administered separately or one or more of the drugs used in the combination protocols can be administered together, such as in an admixture. Where one or more drugs are administered separately, the timing and schedule of administration of each drug can vary. The other therapeutic or diagnostic agents can be administered at the same time as the compounds of the present invention, separately or at different times.

VI. Method of Imaging

In some embodiments, the present invention provides a method of imaging, including administering to a subject to be imaged, an effective amount of a nanocarrier of the present invention, wherein the nanocarrier includes an imaging agent. In other embodiments, the method of treating and the method of imaging are accomplished simultaneously using a nanocarrier having both a drug and an imaging agent.

Exemplary imaging agents include paramagnetic agents, optical probes, and radionuclides. Paramagnetic agents imaging agents that are magnetic under an externally applied field. Examples of paramagnetic agents include, but are not limited to, iron particles including nanoparticles. Optical probes are fluorescent compounds that can be detected by excitation at one wavelength of radiation and detection at a second, different, wavelength of radiation. Optical probes useful in the present invention include, but are not limited to, Cy5.5, Alexa 680, Cy5, DiD (1,1'-dioctadecyl-3,3,3',3'-tetramethylindodicarbocyanine perchlorate) and DiR (1,1'-dioctadecyl-3,3,3',3'-tetramethylindotricarbocyanine iodide). Other optical probes include quantum dots. Radionuclides are elements that undergo radioactive decay.

Radionuclides useful in the present invention include, but are not limited to, $^{3}H$, $^{11}C$, $^{13}N$, $^{18}F$, $^{19}F$, $^{60}Co$, $^{64}Cu$, $^{67}Cu$, $^{68}Ga$, $^{82}Rb$, $^{90}Sr$, $^{90}Y$, $^{99}Tc$, $^{99m}Tc$, $^{111}In$, $^{123}I$, $^{124}I$, $^{125}I$, $^{129}I$, $^{131}I$, $^{137}Cs$, $^{177}Lu$, $^{186}Re$, $^{188}Re$, $^{211}At$, Rn, Ra, Th, U, Pu and $^{241}Am$.

The nanocarriers of the present invention can also be used to detect tumors. For example, the porphyrin groups of the nanocarriers can emit light at a second wavelength after exposure to light at a first wavelength. The emitted light of the second wavelength can then be detected by methods known in the art. The nanocarriers useful for detection of tumors can include metal chelated to the porphyrins, or not include the metal. In some embodiments, the present invention provides a method of detecting a tumor in a subject, including administering to the subject, an effective amount of a nanocarrier of the present invention, exposing the subject to radiation at a first wavelength, wherein the radiation excites porphyrins present on the nanocarrier such that the porphyrins emit radiation at a second wavelength, and detecting the radiation emitted by the excited porphyrins, thereby detecting the tumor.

VII. Examples

Materials

Monomethyl-terminated poly(ethylene glycol) monoamine (MeO-PEG-NH$_2$, M$_w$: 5000 Da) and α-amino-ω-Boc-amino poly(ethylene glycol) (Boc-NH-PEG-NH$_2$, M$_w$: 5000 Da) was purchased from Rapp Polymere (Germany). Pyropheophorbide-a was obtained from Santa Cruz Biotechnology, Inc. (Santa Cruz). Doxorubicin hydrochloride (DOX.HCl) (Novaplus) was obtained from the UC Davis Cancer Center Pharmacy. (Fmoc)lys(Boc)-OH, (Fmoc)Lys(Dde)-OH, (Fmoc)Lys(Fmoc)-OH, (Fmoc)Cys(Trt)-OH and (Fmoc)Ebes-OH were obtained from AnaSpec Inc. (San Jose, Calif.). 3,3'-dihexadecyloxacarbocyanine perchlorate (DiO) and 4,6-diamidino-2-phenylindole (DAPI, blue) were purchased from Invitrogen. Cholic acid, MTT [3-(4,5-dimethyldiazol-2-yl)-2,5 diphenyl tetrazolium bromide], Ellman's reagent [DTNB, 5,59-dithiobis(2-nitrobenzoic acid)] and all other chemicals were purchased from Sigma-Aldrich (St. Louis).

PLZ4 (amino acid sequence: cQDGRMGFc in which upper case letters represent L-amino acids and lowercase letters represent unnatural D-cysteines used to cyclize and stabilize PLZ4) were prepared via solid phase peptide synthesis on Rink resin as described previously (Bioconjug Chem 21, 1216-1224 (2010); Biomaterials 30, 6006-6016 (2009); Urol Oncol Epub ahead of print (2012)).

Statistical analysis was performed by Student's t-test for two groups, and one-way ANOVA for multiple groups. All results were expressed as the mean±standard error (SEM) unless otherwise noted. A value of P<0.05 was considered statistically significant.

Example 1

Synthesis of Telodendrimer

The telodendrimers were synthesized via solution-phase condensation reactions using Meo-PEG-NH$_2$, Boc-NH-PEG-NH$_2$, lysine, cholic acid and pyropheophorbide-a as building blocks as reported previously (Bioconjug Chem 21, 1216-1224 (2010); Biomaterials 30, 6006-6016 (2009)).

To synthesize PLZ4-telodendrimers, an aqueous-phase "click chemistry" catalyzed by cuprous ion was performed to couple the alkyne group on PLZ4 peptides to the azide group at the end of PEG on our previously reported telodendrimer (PEG$^{5k}$-CA$_8$) at a molar ratio of 1:2 (PLZ4: PEG). After conjugation, no PLZ4 was detected, suggesting PLZ4 had been successfully conjugated to the telodendrimer.

Figure 2:
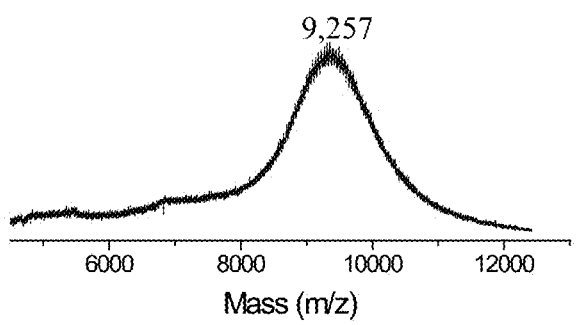
FIG. 2 shows the MALDI-TOF MS of $PEG^{5k}\text{-}Por_4\text{-}CA_4$ telodendrimer.
Figure 4:
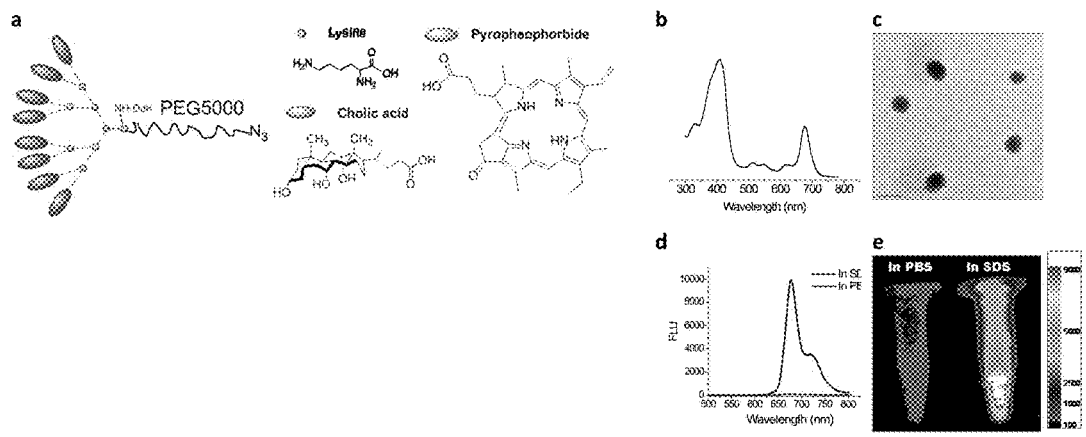
FIG. 4 shows (a) Schematic illustration of a representative porphyrin-containing telodendrimer ($PEG^{5k}\text{-}Por_4\text{-}CA_4$), comprised of 4 pyropheophorbides and 4 cholic acids attached to the terminal end of a linear PEG chain. The azido (—$N_3$) group at the distal end of PEG will be used for conjugation to PLZ4. (b) Absorbance and (c) TEM imaging of the porphyrin-based micelles (Scale bar: 50 nm). (d) The fluorescence emission spectra of the porphyrin-based micelles in the presence of PBS (red) and SDS (blue). EX: 405 nm. (e) Near-infrared fluorescence imaging of the porphyrin-based micelles in the absence and in the presence of SDS using a Kodak imaging station (micelle concentration: 1 mg/mL). In micelles, porphyrin is quenched. SDS dissociates micelles and porphyrin emits fluorescence upon excitation at 405 nm.
Figure 5:
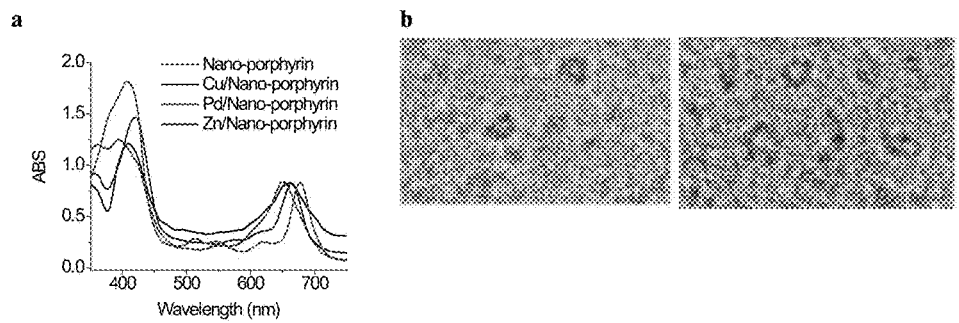
FIG. 5 shows (a) The absorbance spectra of the NP after chelating different metal ions (b). NP loaded with Cu(II) viewed with cryo-EM at magnification of 80,000×.

The pyropheophorbide-a containing telodendrimers were synthesized by replacing 4 of the 8 cholic acids of telodendrimer (PEG$^{5k}$-CA$_8$, nomenclature: 5000 dalton PEG with 8 cholic acids) with 4 pyropheophorbides to form PEG$^{5k}$-Por$_4$-CA$_4$ (FIG. 4) using stepwise solution peptide chemistry. Briefly, (Fmoc)lysine(Fmoc)-OH (2 equiv) was coupled onto the N-terminal of PEG using diisopropyl carbodiimide (DIC, 2 equiv) and N-hydroxybenzotriazole (HOBt, 2 equiv) as coupling reagents in DMF overnight. The completion of the coupling was confirmed by Kaiser test: yellow color indicates no amino group left, blue color indicates the presence of amino groups. PEGylated molecules were precipitated by adding ice-cold ether and washed with ice-cold ether twice. Fmoc groups were removed by the treatment with 20% piperidine in DMF, and the PEGylated molecules were precipitated and washed three times by cold ether. The precipitate was dried under vacuum and one additional coupling of (Fmoc)lysine(Fmoc)-OH and one coupling of (Fmoc)lysine(Boc)-OH were carried out subsequently to generate a third generation of dendritic polylysine on one end of PEG. Cholic acid NHS ester, prepared according to the literature, was then coupled to the terminal end of dendritic polylysine after Boc deprotection using TFA/DCM (1:1, v/v). Finally, pyropheophorbide-a was coupled to the terminal end of dendritic polylysine after Fmoc deprotection, resulting in PEG$^{5k}$-Por$_4$-CA$_4$. The telodendrimer was precipitated and washed by cold ether and dissolved in water. The telodendrimer solution was filtered and then dialyzed against 4 L water in a dialysis tube with MWCO of 3.5 KDa; reservoir water was refreshed completely four times in 24 h. Finally, the telodendrimer was lyophilized. The molecular weight of PEG$^{5k}$-Por$_4$-CA$_4$ was collected on ABI 4700 MALDI TOF/TOF mass spectrometer (linear mode) using R-cyano-4-hydroxycinnamic acid as a matrix. The mono-dispersed mass traces were detected for the telodendrimers, and the molecular weight of the telodendrimer from MALDI-TOF MS (FIG. 2) was almost identical to the theoretical value.

Figure 3:
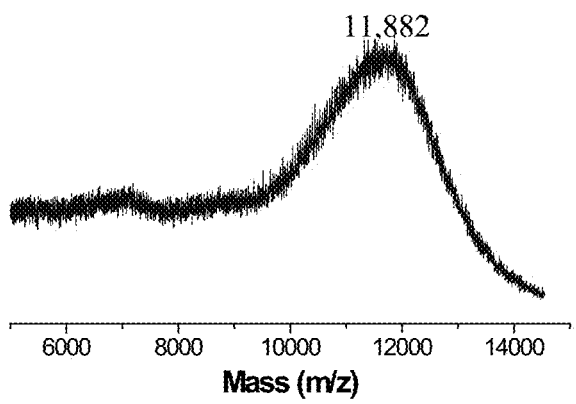
FIG. 3 shows the MALDI-TOF MS of $PEG^{5k}\text{-}Cys_4\text{-}L_8\text{-}CA_8$ telodendrimer comparing with the starting PEG 5000 and $PEG^{5k}\text{-}CA_8$ telodendrimer.
Figure 6:
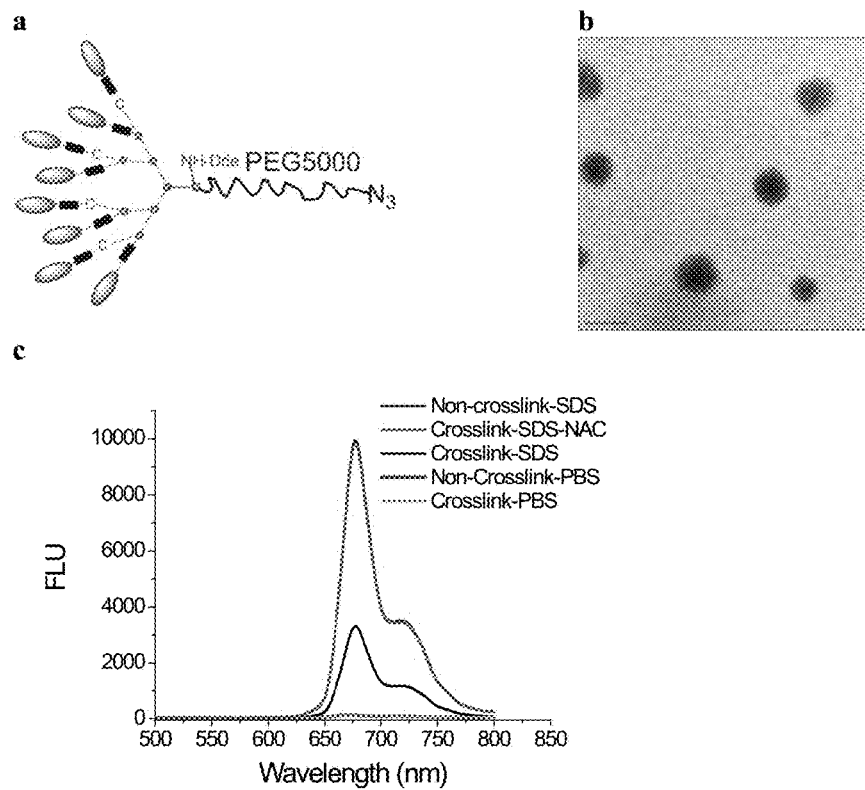
FIG. 6 shows (a) Schematic illustration of a representative porphyrin-containing telodendrimer (PEG$^{5k}$-Cys$_4$-Por$_4$-CA$_4$), comprised of 4 cysteines, 4 pyropheophorbides and 4 cholic acids attached to the terminal end of a linear PEG chain. (b) TEM imaging of the disulfide crosslinked porphyrin-based micelles (Scale bar: 50 nm). (c) The fluorescence emission spectra of the disulfide crosslinked porphyrin-based micelles in the presence of PBS and SDS in the comparison with the non-crosslinked porphyrin-based micelles. EX: 405 nm.
Figure 7:
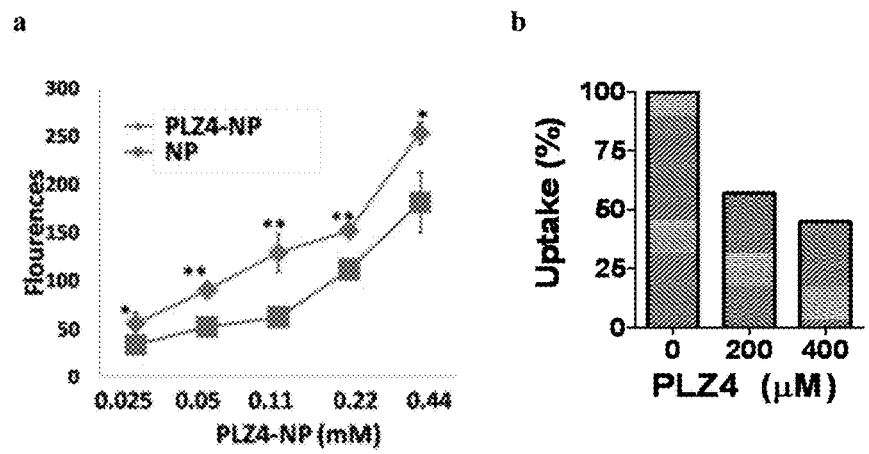
FIG. 7 (a) shows cellular uptake of non-targeting NP vs PLZ4-NP into 5637 human bladder cancer cells after 4 hr incubation. (b) K9TCC-Pu—In cells were preincubated with free PLZ4 peptide for one hr and followed by incubation with 2.2 µM of PLZ4-NP for another hr. Cells without free PLZ4 treatment were served as 100% control. Cells were fixed in formalin and analyzed by flow cytometry.
Figure 8:
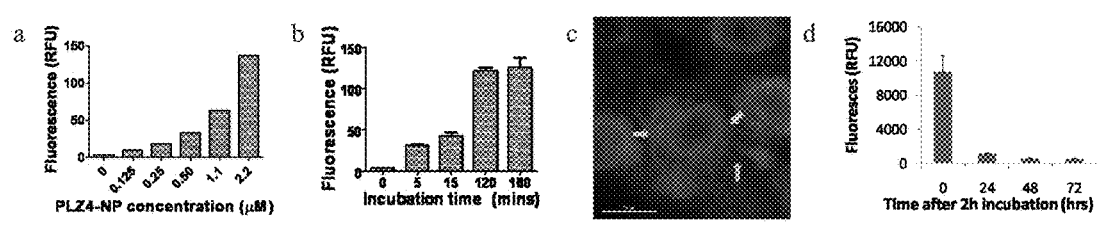
FIG. 8 shows cellular uptake of PLZ4-NP by K9TCC-Pu—In bladder cancer cells as a function of (a) PLZ4-NP concentration (4 hr incubation), and (b) time (2.2 µM PLZ4-NP). (c) Human bladder cancer cell line 5637 was incubated with 2.2 µM of PLZ4-NP for 20 min in a glass bottom dish. After adding DAPI containing medium for nucleus staining, live cell imaging was acquired using high resolution topography imaging system (Delta vision). Arrows indicated the membrane distribution. (d) 5637 was treated with 2.2 µM of PLZ4-NP for 2 hr. After washed, cells were than cultured for another 0, 24, 48, and 72 hr in fresh complete medium. Cells were than trypsinzed and fixed in 10% formal before test and cells were analyzed by flow cytometry.
Figure 9:
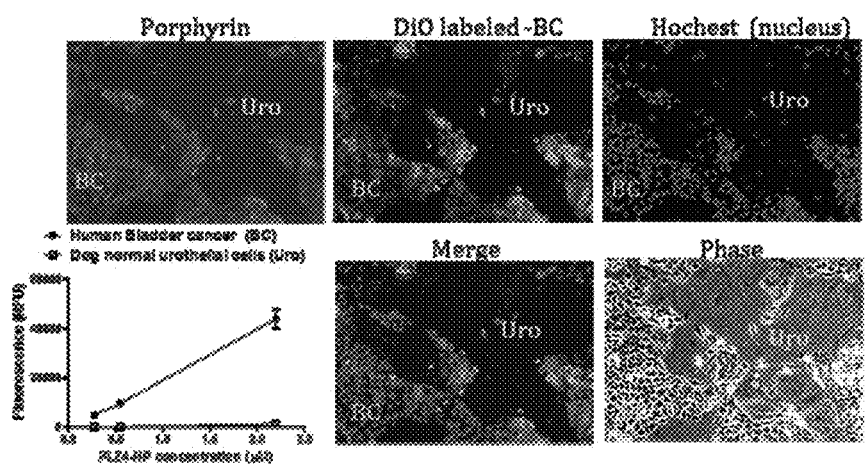
FIG. 9 shows PLZ4-NP specific uptake by bladder cancer cells but not normal urothelial cells. Co culture of normal canine urothelial cells (Uro) with pre DiO labeled human bladder cancer cell line 5637(BC) was treated with PLz4-NP for 2 hours. (pophryin: red; DiO: green; Hochest: blue) (100×)
Figure 10:
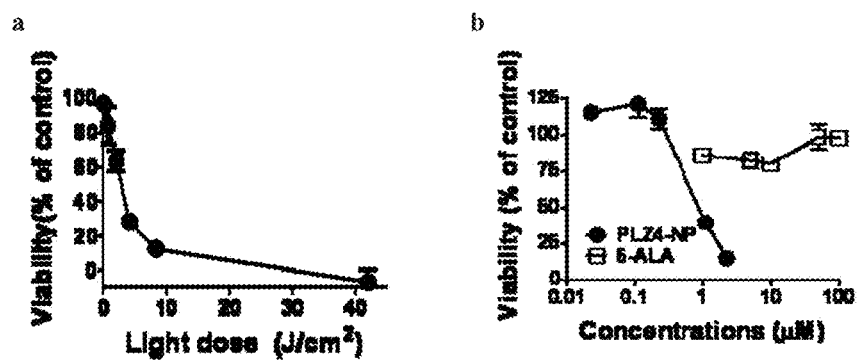
FIG. 10 shows cytotoxicity of 5637 bladder cancer cells after (a) 2 hrs exposure to 2.2 µM PLZ4-NP followed by illumination with various level of light (red light, 650 nm wave length), and (b) incubation with PLZ4-NP or 5-ALA for 2 hrs followed by exposure to 4.2 J/cm2 of red light.
Figure 11:
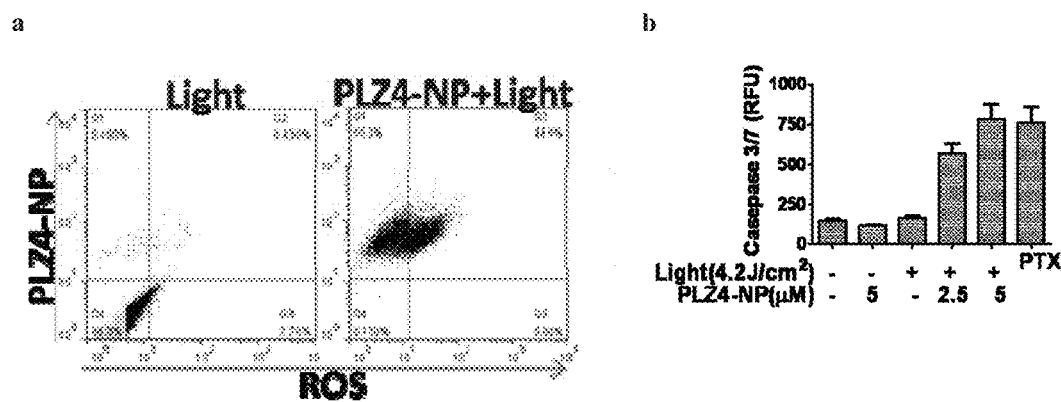
FIG. 11 shows ROS mediated cell death after PZL4-NP and PDT treatment of 5637 human bladder cancer cells (a) cells were treated with or without 2.2 µM PZL4-NP for 2 hr and loaded with aminophenyl fluorescein (APF; an ROS indicator) for 30 min. After that, cells were treated with PDT at 4.2 J/cm$^2$ and analyzed with flow cytometry; (b) cells were treated with different concentrations of PZL4-NP for 2 hr followed by PDT. 24 hr later, caspase3/7 activity was measured by SensoLyte® Kit (Anaspec, Fremont, Calif.). (PTX is paclitaxel treatment as a positive control for apoptosis)
Figure 12:
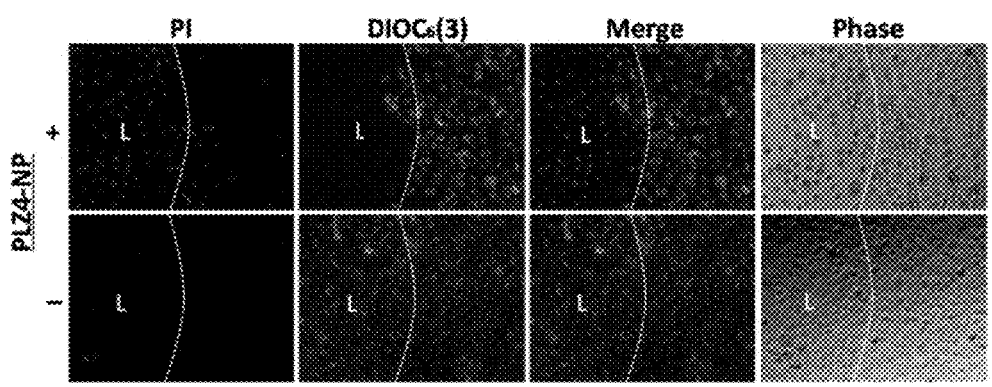
FIG. 12 shows 5637 cells were incubated with 2.2 µM PZL4-NP for 2 hr in 96-well black-wall plate, stained with 40 nM of DiOC$_6$(3) (Green, ΔΨm$^{high}$) for 20 min in the end of incubation to evaluate mitochondria membrane potential (ΔΨm), and followed by illumination of a portion of each well to elicit PDT effect. 24 hr later, the cells were stained with propridium iodide for cell death.
Figure 13:
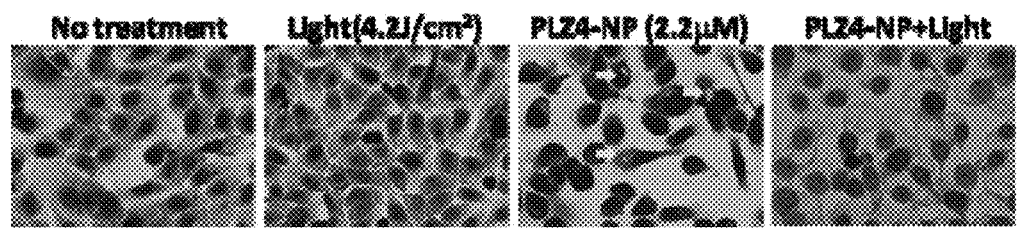
FIG. 13 shows cell morphology after PDT. 5637 cells were cultured on the 8-well chamber slides and treated for 2 hr with none, light alone (4.2 J/cm$^2$), PLZ4-NP alone or combination of PLZ4-NP and light (PDT), or T-PN for two hr followed by PDT. Cells were then fixed and stained with Hema3®.
Figure 14:
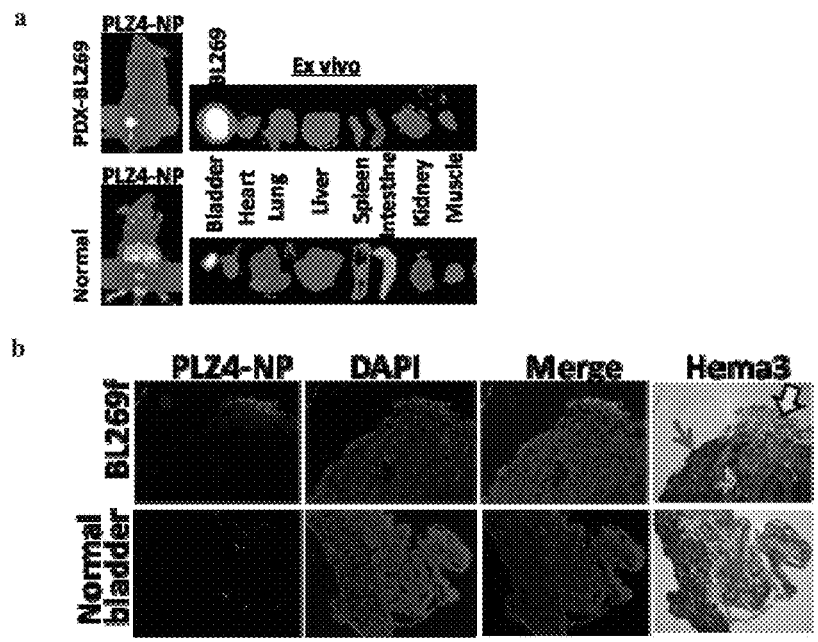
FIG. 14 shows selective uptake of PLZ4-NP into an orthotopic human bladder cancer xenograft model after intravesical administration into nude mouse. (a) Human patient derived xenograft (PDX) BL269f was established in NSG mice. Mouse orthotopic model of BL269f was generated by directly injected suspension BL269f cells into bladder wall. After 4 weeks, the growth of solid tumor was noted with decreased bladder lumen capacity. We injected 30 µl of PLZ4-NP into bladder for 2 hr under general anesthesia. Bladder was washed with PBS and isolated outside of body for in vivo imaging. Afterwards, mice were immediately sacrificed and major organs were dissected for ex vivo imaging. Similar experiments were done in normal NSG mice without bladder tumor transplantation. (b) Bladders with or without BL269f xenograft were fixed in O.C.T and 10 microns thick of cryosections were obtained. Nucleus was counter stained by DAPI (blue), and intracellular PLZ4-NP fluoresce red. After fluorescent imaging study, the tissue was re-stained with Hema3®. (yellow arrow: exposed bladder cancer tissue, red arrow: intact normal urothelial cells.) (40×)
Figure 15:
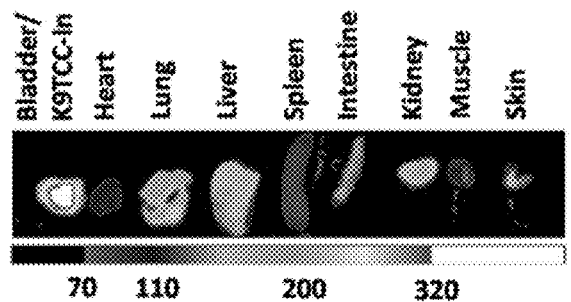
FIG. 15 shows ex vivo near infra-red imaging of tumor/bladder and organs 24 hr after iv administration of non-crosslinked PLZ4-NP.
Figure 16:
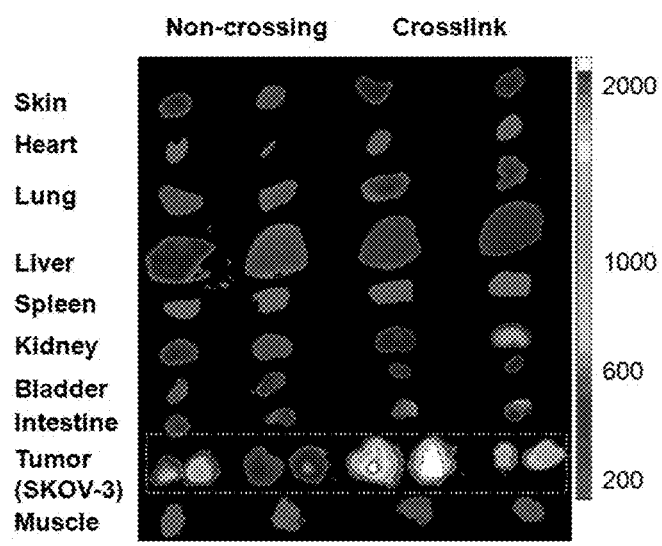
FIG. 16 shows ex vivo near infra-red imaging of tumor and organs of mice bearing Skov-3 ovarian cancer xenograft 24 hr after iv administration of non-crosslinked NP and crosslinked NP. Relative fluorescence color scale bar shown.
Figure 17:
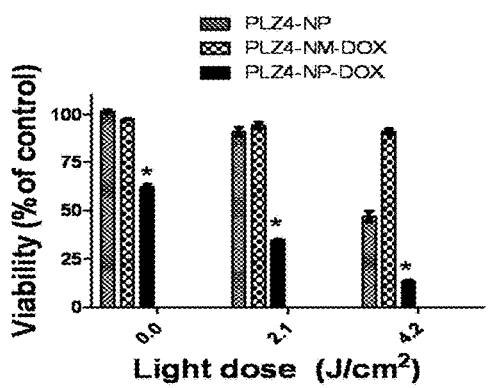
FIG. 17 shows cytotoxicity effect in combination of doxorubicin with PLZ4-NP mediated PDT. (a) 5637 cells were treated with PLZ4-NP, PLZ4-NP-Dox or PLZ4-NM-Dox at the concentration of 1 µg/ml Doxorubicine and/or 2.2 µM porphyrin for 2 hours. After wash, cells were exposed without or with light at 2.1 and 4.2 J/cm2. Cell viability was measured after 48 hours. * p<0.05 (b) 5637 cells were treated with PLZ4-NP, PLZ4-NP-Dox, free Dox, Doxil, PLZ4-NM-Dox, and a combination of PLZ4-NP and PLZ4-NM-Dox for 5 minutes and 2 hours. Intracellular doxorubicin concentration was evaluated with flow cytometry. This results present at mean+/−SD from 3 different independent experiments. * p<0.05; ** p<0.01 (c) 5637 cells were treated with PLZ4-NP (PNP), PLZ4-NM-DOX (PN-DOX), a combination of PNP and PN-DOX, and PLZ4-NP-DOX (PNP-DOX) for 2 hours. Porphrin (red) and doxorubicine (green) were detected by fluoresces microscope. (100×) (d) Sub-cellular distribution of PLZ4-NP-DOX (PNP-DOX) was detected by confocal microscope. (600× oil) at 5 mintues, 1 and 3 hours. Cells were washed but not fixed. PNP (porphyrin: red), Doxorubicin (green)
Figure 17:
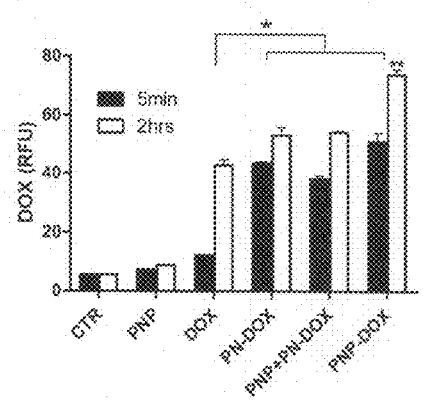
Figure 17:
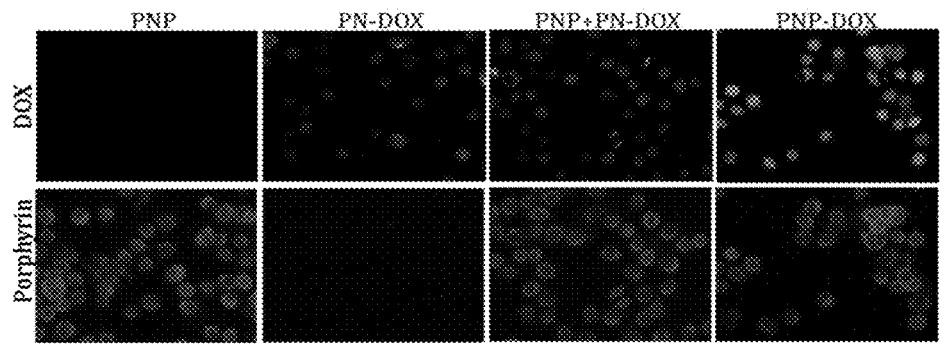
Figure 17:
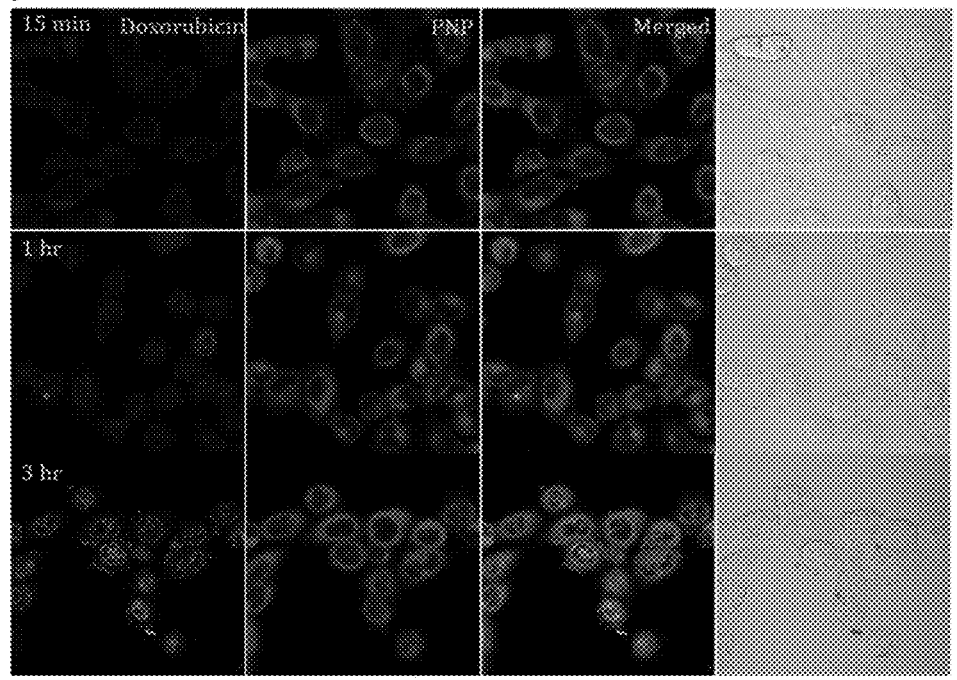
Figure 18:
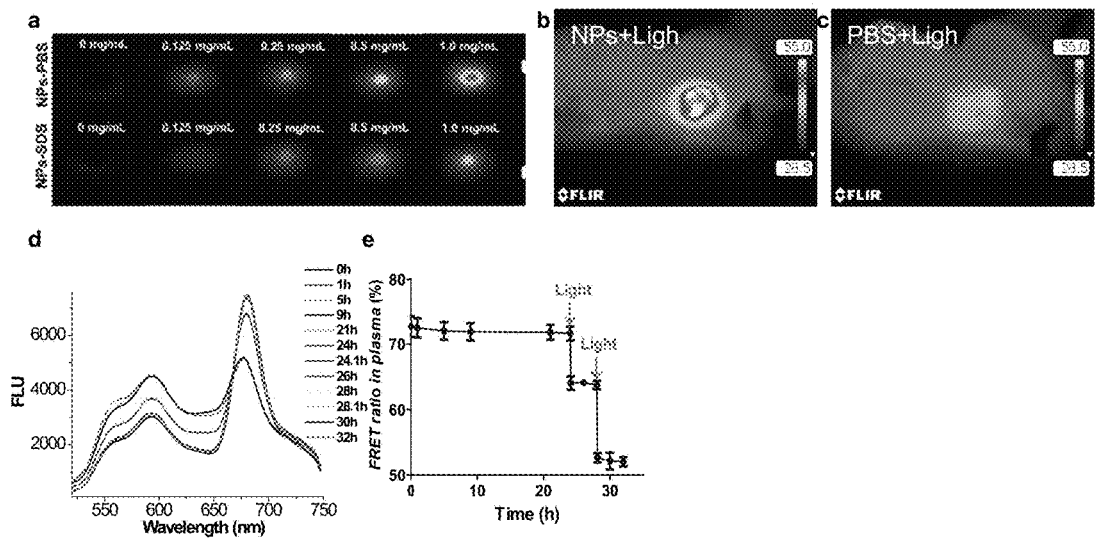
FIG. 18 shows (a) Concentration-dependent photo-thermal effect of nanoporphyrins. The temperature was monitored by a thermal camera. Irradiation time: 20 s. Tumor temperature change in transgenic mice after 60 s light irradiation at 24 hrs post-injection of (b) nanoporphyrins and (c) PBS. (d) FRET signal of doxorubicin loaded nanoporphyrins (NPs-DOX) in human plasma treated with light at 24 hrs and 28 hrs, respectively. (e) The changes in FRET ratio of NPs-DOX. Irradiation time: 5 min.
Figure 19:
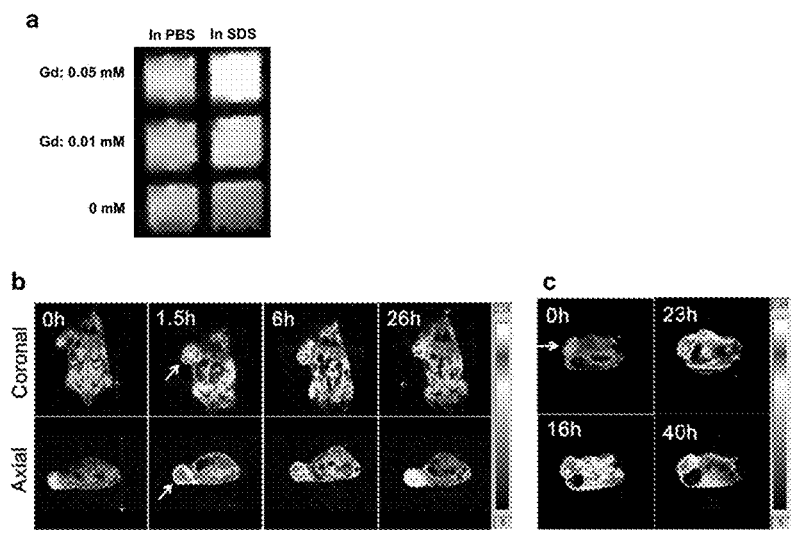
FIG. 19 shows (a) The in vitro MRI signal of GNP in the absence and in the presence of SDS obtained by T1-weighted spin-echo MR imaging on a Bruker Biospec 7T MRI scanner. (b) The Coronal and Axial MR images of transgenic mice with mammary cancer (FVB/n Tg(MMTV-PyVmT) by a FLASH sequence pre-injection and after injection with 0.15 mL GNP (Gd dose: 0.015 mmole/kg). The white arrow points to the tumor site. (c) The Axial MRI images of Skov-3 ovarian cancer xenograft injected with 0.2 mL GNP (Gd dose: 0.02 mmole/kg) obtained by a FLASH sequence. The white arrow points to the tumor site.
Figure 20:
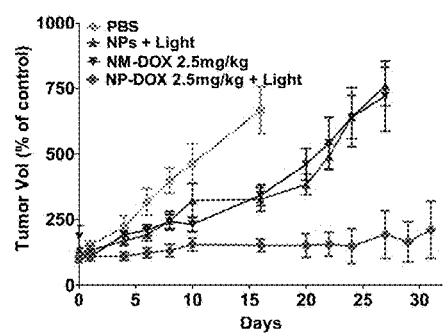
FIG. 20 shows the tumor volume change of (a) mice (n=8) bearing Skov-3 ovarian cancer xenograft and (b) transgenic mice with mammary cancer (FVB/n Tg(MMTV-PyVmT) (n=8), treated with nanoporphyrins (NPs) and doxorubicin loaded nanoporphyrins (NP-DOX) at day 0 and 8 followed by exposure to light (690 nm) at 24 hr post injection. PBS Doxorubicin loaded standard nano-micelles (NM-DOX) were injected for comparison. DOX dose: 2.5 mg/kg, porphyrin dose: 5.0 mg/kg, light dose: 24 J/cm$^2$ for Skov-3 model and 60 J/cm$^2$ for transgenic model, respectively. (c) Pictures of transgenic mice at day 34 of the treatment. Relative fluorescence color scale bar shown.
Figure 20:
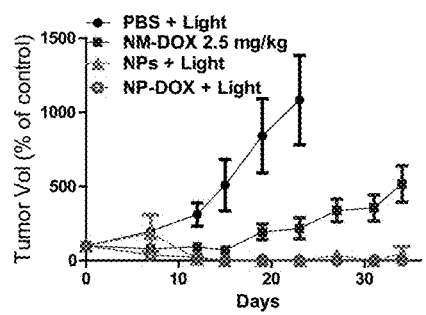
Figure 20:
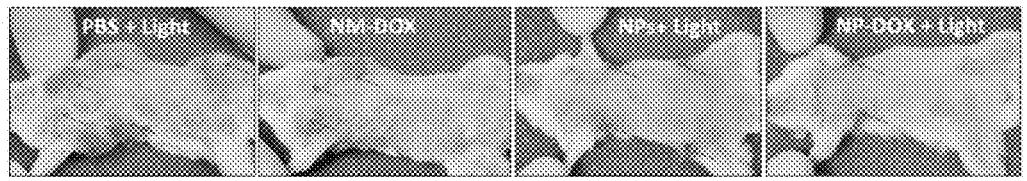

The thiolated pyropheophorbide-a telodendrimer (named as PEG$^{5k}$-Cys$_4$-Por$_4$-CA$_4$, FIG. 6a) was synthesized by replacing 4 of the 8 cholic acids of our previously reported thiolated telodendrimer (PEG$^{5k}$-Cys$_4$-L$_8$-CA$_8$) using the same strategy. The typical procedure for synthesis of PEG$^{5k}$-Cys$_4$-Por$_4$-CA$_4$ was as follows: (Fmoc)Lys(Fmoc)-OH (3 eq.) was coupled onto the N terminus of PEG using DIC and HOBt as coupling reagents until a negative Kaiser test result was obtained, thereby indicating completion of the coupling reaction. PEGylated molecules were precipitated by adding cold ether and then washed with cold ether twice. Fmoc groups were removed by the treatment with 20% (v/v) 4-methylpiperidine in dimethylformamide (DMF), and the PEGylated molecules were precipitated and washed three times by cold ether. White powder precipitate was dried under vacuum and one coupling of (Fmoc)Lys(Fmoc)-OH and one coupling of (Fmoc)lys(Dde)-OH were carried out respectively to generate a third generation of dendritic polylysine terminated with four Dde and Fmoc groups on one end of PEG. Then the Fmoc groups were removed. Fmoc)Cys(Trt)-OH, (Fmoc)Ebes-OH and Cholic acid NHS ester (12 equiv) [38] were coupled step by step to the terminal end of dendritic polylysine. After the removal of Dde protecting group by 2% (v/v) hydrazine in DMF, (Fmoc)Ebes-OH and pyropheophorbide-a (12 equiv) were coupled subsequently to the leftover amino groups on the terminal end of dendritic polylysine. The Trt groups on cysteines were removed by TFA/H$_2$O/ethanedithiol (EDT)/triethylsilane (TIS) (94:2.5:2.5:1, v/v) resulting in PEG$^{5k}$-Cys$_4$-Por$_4$-CA$_4$ thiolated telodendrimer (FIG. 3). The thiolated telodendrimer was recovered from the mixture by three cycles of dissolution/reprecipitation with DMF and ether, respectively. Finally, the thiolated telodendrimer was dissolved in acetonitrile/water and lyophilized.

Ellman's test was used to determine the number of cysteines conjugated to telodendrimers by free thiol groups. After adding Ellman reagents to a standard thiol (cysteine) for 15 min, a calibration curve was prepared by plotting the absorbance at 412 nm as function of cysteine concentrations. Based on the calibration curve, the number of cysteines on the telodendrimers was calculated from the absorbance of samples in Ellman's test. As determined by quantitative Ellman's test, the number of covalently attached cysteines in PEG$^{5k}$-Cys$_4$-Por$_4$-CA$_4$ was 4.03, which was consistent with the molecular formula of the target telodendrimer. The molecular weight of PEG$^{5k}$-Cys$_4$-Por$_4$-CA$_4$ was collected on ABI 4700 MALDI TOF/TOF mass spectrometer (linear mode) using R-cyano-4-hydroxycinnamic acid as a matrix. The mono-dispersed mass traces were detected for the starting PEG and the telodendrimers, and the molecular weights of the telodendrimers from MALDI-TOF MS (FIG. 3) were almost identical to the theoretical value.

Example 2

Generation of Metallic Telodendrimers

To generate telodendrimers with a chelated metal, 10 fold excess free metal ions were incubated with telodendrimers in methanol for 1 hour at room temperature under nitrogen. Free metal was removed with by filter column with a molecular weight cut off of 3,500. The metal porphyrin-lipid was then aliquoted, dried and stored under argon at −20° C.

Example 3

Preparation of Nano-Porphyrin Micelles

To make targeting micelles, PLZ4-conjugated telodendrimers(PLZ4-PEG$^{5k}$-CA$_8$) were mixed with PEG$^{5k}$-Por$_4$-CA$_4$. After self-assembly, the more hydrophilic targeting PLZ4 ligands were displayed on the surface of micelles.

In order to make disulfide crosslinked micelles, 20 mg total amount of PEG$^{5k}$-Cys$_4$-Por$_4$-CA$_4$ and PEG$^{5k}$-Cys$_4$-L$_8$-CA$_8$ was dissolved in 1 mL phosphate buffered saline (PBS) to form micelles and then sonicated for 10 min. The thiol groups on the telodendrimer were oxidized to form disulfide linkages by hydrogen peroxide. The level of free thiol groups were monitored by Ellman's test over time. The micelle solution was used for further characterizations without dialysis after the level of free thiol groups remained at a constant low value.

Preparation of Drug Loaded Micelles

Doxorubicin was loaded into the micelles by the solvent evaporation method as described previously. Before the encapsulation of DOX into the polymeric micelles, DOX.HCl was stirred with 3 molar equivalent of triethylamine in chloroform (CHCl3)/methanol (MeOH) (1:1, v/v) overnight to remove HCl from DOX.HCl. 20 mg telodendrimer along with different amount of neutralized DOX were first dissolved in CHCl3/MeOH, mixed, and evaporated on rotavapor to obtain a homogeneous dry polymer film. The film was reconstituted in 1 mL phosphate buffered solution (PBS), followed by sonication for 30 min, allowing the sample film to disperse into micelle solution. To track their in vivo fates, hydrophobic NIRF dye DiD was encapsulated into the micelles using the same method as described above. Finally, the micelle formulation was filtered with 0.22 μm filter to sterilize the sample. To determine the amount of DOX, DOX-loaded micelles were diluted with DMSO (micelle solution/DMSO: 1:9, v/v) to dissociate micelle nanoparticles and the fluorescence was measured by NanoDrop 2000 spectrophotometer (Thermo Scientific), wherein calibration curve was obtained using a series of DOX/DMSO standard solutions with different concentrations. The DOX loaded disulfide crosslinked micelles were prepared via the same method followed the oxidation of the thiols to form intramicellar disulfide bonds by hydrogen peroxide.

Characterization of Micelles

The size and size distribution of the micelles were measured by dynamic light scattering (DLS) instruments (Microtrac). The micelle concentrations were kept at 1.0 mg/mL for DLS measurements. The zeta potential of these micelles was measured by DLS using the function of Zetatrac (Microtrac). All measurements were performed at 25° C., and data were analyzed by Microtrac FLEX Software 10.5.3. The morphology of micelles was observed on a Philips CM-120 transmission electron microscope (TEM). The aqueous micelle solution (1.0 mg/mL) was deposited onto copper grids, stained with phosphotungstic acid, and measured at room temperature. The absorbance and the fluorescence signal of the micelles were measured by NanoDrop spectrophotometer (Thermo Scientific).

Example 4

Treatment of Human Ovarian Cancer and Bladder Cancer Cells

SKOV-3 human ovarian cancer cell lines and 5637 human bladder cancer cell lines were purchased from ATCC and maintained with the recommended medium. The dog bladder cancer cell line, K9TCC-Pu—In, was originally developed and directly provided by Dr. Deborah Knapp at Purdue University in July, 2009. These cell lines were tested and authenticated using the morphology, immunohistochemistry, gene expression and tumorigenicity assays in Dr. Knapp's lab in 2009. Because these cells were obtained directly from Dr. Knapp, who performed cell line characterizations, and passaged in the user's laboratory for less than 6 months after resuscitation, re-authorization was not required.

Cell Uptake of Nano-Porphyrins

The cancer cells were seeded in eight-well tissue culture chamber slides (BD Biosciences, Bedford, Mass., USA), followed by 24 h of incubation in cell culture medium containing 10% FBS. The medium was replaced, and nano-porphyrin micelles were added to each well. At pre-determined time points, the cells were washed three times with PBS, fixed with 4% paraformaldehyde and the cell nuclei were stained with DAPI. The slides were mounted with cover slips and observed by a DeltaVision imaging system (AppliedPrecision, CA) per manufacturer's protocol.

In another set of experiments, canine urothelial cells were cultured in the complete medium (10% FBS in RPMI1640 with antibiotics) for 3 days until 60% confluence. Human bladder cell line 5637 was pre-stained with DiO (400 nM) for 20 minutes and co-cultured in the same plate with urothelial cells overnight. 2.2 µM of PLZ4-NP was added and cell imaging was acquired by a DeltaVision imaging system.

Example 5

In Vitro Photodynamic Therapy (PDT)

K9TCC-Pu—In and 5637 bladder cancer cell lines and SKOV-3 ovarian cancer cell lines were used to evaluate the photosensitizing function of nano-porphyrins. We first treated the cancer cells with 2.2 µM nano-prophyrins for 2 hr. After thorough washing, the cells were exposed to red light (650 nm). Cell viability was determined using WST-8 proliferation kit (Caymen) 24 hr after illumination. 5-aminolevulinic acid (5-ALA), the traditional photodynamic diagnosis/therapy agent, was used as a control. In another experiments, DOX loaded nanoporphyrins were used to treat the cancer cells followed by light exposure. The cells were also treated with telodendrimers and empty crosslinked micelles with different dilutions and incubated for total 72 h in the absence of light exposure in order to evaluate the dark toxicity and telodendrimer related toxicity.

Animal and Tumor Xenograft Model

Female athymic nude mice (Nu/Nu strain), 6-8 weeks age, were purchased from Harlan (Livermore, Calif.). All animals were kept under pathogen-free conditions according to AAALAC guidelines and were allowed to acclimatize for at least 4 days prior to any experiments. All animal experiments were performed in compliance with institutional guidelines and according to protocol No. 07-13119 and No. 09-15584 approved by the Animal Use and Care Administrative Advisory Committee at the University of California, Davis. The subcutaneous xenograft model of ovarian cancer was established by injecting $7 \times 10^6$ SKOV-3 ovarian cells in a 100 µL of mixture of PBS and Matrigel (1:1 v/v) subcutaneously into the right flank of female nude mice.

Establishment of patient-derived xenografts: The animal protocol was approved by the UC Davis Institutional Animal Care and Use Committee (IACUC) before experiments were performed. To establish subcutaneous patient-derived xenografts (PDX), NOD SCID gamma (NSG; The Jackson Laboratory, West Sacramento, Calif.) 4-5 week-old mice were used. Fresh, unmanipulated clinical tumor fragments (3-5 mm$^3$) were loaded into a trochar with sterile forceps. The loaded trochar was then gently pushed into the flank skin and the trochar plunger was depressed to eject the tumor fragments. The trochar was gently removed and the injection area was sterilized.

To generate an orthotopic xenograft model in NSG mice, a passage #1 PDX specimen was harvested and cut into small pieces. After treated with 1 ml of Accutase (Innovative Cell Technology, San Diego, Calif.) for 30 minutes at 37° C., single cell suspensions were obtained after filtering through cell strainers (BD Falcon, Canaan, Conn.) to remove larger tissues. Cells in 5-10 µl PBS were then injected into mouse bladder walls while visually locating the bladder under general anesthesia. Mice were monitored every day after the surgery.

Example 6

Biodistribution of the Nano-Porphyrins

K9TCC-Pu—In and 5637 bladder cancer and SKOV-3 ovarian cancer xenograft mice models with subcutaneous tumor of an approximate 8~10 mm diameter were subjected to in vivo NIRF optical imaging. At different time points post injection of nano-porphorin micelles, mice were scanned using a Kodak multimodal imaging system IS2000MM with an excitation bandpass filter at 625 nm and an emission at 700 nm. The mice were anaesthetized by intraperitoneal injection of pentobarbital (60 mg/kg) before each imaging. After in vivo imaging, animals were euthanized by $CO_2$ overdose at 24, 48 and 72 h after injection. Tumors and major organs were excised and imaged with the Kodak imaging station.

NIRF imaging studies was performed in the orthotopic xenograft model in NSG mice. Briefly, female NSG mice bearing orthotopic human bladder cancers or normal NSG mice were intravesically injected with 30 µl of PLZ4-NP via urethra under general anesthesia. After 2 hr of incubation, the bladder was isolated for whole body in vivo imaging using Kodak imaging system.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. A compound having a structure:

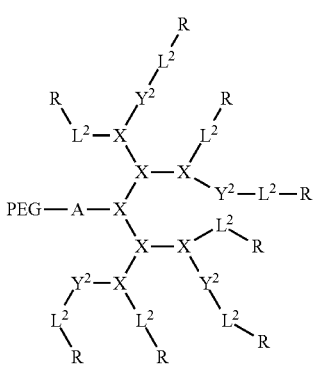

wherein
each PEG is a polyethyleneglycol (PEG) polymer having a molecular weight of 1-100 kDa;
A comprises at least one branched monomer unit X and is linked to at least one PEG group;
X is a diamino carboxylic acid;
each $Y^2$ is independently:
absent; or
a crosslinkable group independently selected from the group consisting of boronic acid, dihydroxybenzene and a thiol,
wherein at least two $Y^2$ are present;
each $L^2$ is independently a bond or a linker; and at least one R group is a porphyrin, and each remaining R is independently selected from the group consisting of cholic acid, (3a,5b,7a,12a)-7,12-dihydroxy-3-(2,3-dihydroxy-1-propoxy)-cholic acid (CA-4OH), (3α, 5β, 7α, 12α)-7-hydroxy-3,12-di(2,3-dihydroxy-1-propoxy)-cholic acid (CA-5OH), and (3α, 5β, 7α, 12α)-7,12-dihydroxy-3-(3-amino-2-hydroxy-1-propoxy)-cholic acid (CA-3OH—NH$_2$).

2. The compound of claim 1, wherein A comprises at least one branched monomer unit X independently selected from the group consisting of a diamino carboxylic acid, a dihydroxy carboxylic acid and a hydroxyl amino carboxylic acid.

3. The compound of claim 1, wherein each diamino carboxylic acid is independently selected from the group consisting of 2,3-diamino propanoic acid, 2,4-diaminobutanoic acid, 2,5-diaminopentanoic acid (ornithine), 2,6-diaminohexanoic acid (lysine), (2-Aminoethyl)-cysteine, 3-amino-2-aminomethyl propanoic acid, 3-amino-2-aminomethyl-2-methyl propanoic acid, 4-amino-2-(2-aminoethyl) butyric acid and 5-amino-2-(3-aminopropyl) pentanoic acid.

4. The compound of claim 1, wherein each branched monomer unit X is lysine.

5. The compound of claim 1, wherein linker $L^2$ when present has the formula:

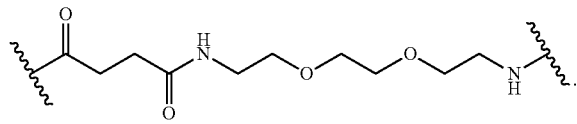 [SMILES: *NCCOCCOCCNC(=O)CCC(*)=O]

6. The compound of claim 1, wherein each remaining R is cholic acid.

7. The compound of claim 1, having the structure:

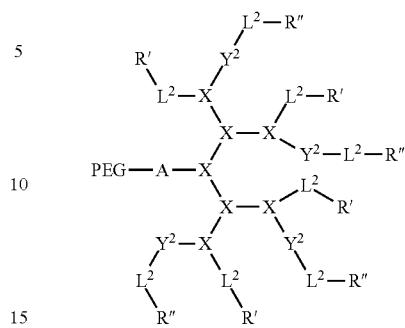

wherein
PEG is PEG5k;
each branched monomer unit X is lysine;
A is lysine;
each $L^2$ is a bond or linker Ebes;
each $Y^2$ is absent or is cysteine, wherein at least two $Y^2$ groups are cysteine; and at least one R group is a porphyrin, and each remaining R is independently selected from the group consisting of cholic acid (CA), (3α, 5β, 7α, 12α)-7,12-dihydroxy-3-(2,3-dihydroxy-1-propoxy)-cholic acid (CA-4OH), (3α, 5β, 7α, 12α)-7-hydroxy-3,12-di(2,3-dihydroxy-1-propoxy)-cholic acid (CA-5OH) and (3α, 5β, 7α, 12α)-7,12-dihydroxy-3-(3-amino-2-hydroxy-1-propoxy)-cholic acid (CA-3OH—NH$_2$).

8. The compound of claim 7, wherein the compound has the structure

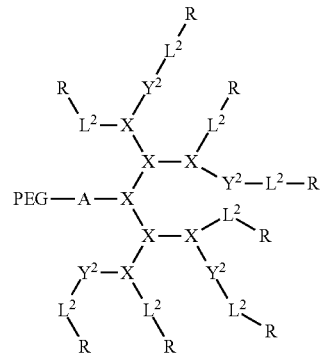

wherein
each R' is selected from the group consisting of cholic acid (CA), (3α, 5β, 7α, 12α)-7,12-dihydroxy-3-(2,3-dihydroxy-1-propoxy)-cholic acid (CA-4OH), (3α, 5β, 7α, 12α)-7-hydroxy-3,12-di(2,3-dihydroxy-1-propoxy)-cholic acid (CA-5OH), (3α, 5β, 7α, 12α)-7,12-dihydroxy-3-(3-amino-2-hydroxy-1-propoxy)-cholic acid (CA-3OH—NH$_2$); and
each R" is a porphyrin selected from the group consisting of pyropheophorbide-a, pheophorbide, chlorin e6, purpurin and purpurinimide.

9. The compound of claim 8, wherein the compound is selected from the group consisting of:
(1) each $L^2$ is a bond, each $Y^2$ is cysteine, each R' is cholic acid, and each R" is pyropheophorbide-a; and
(2) each $L^2$ is the linker Ebes, each $Y^2$ is cysteine, each R' is cholic acid, and each R" is pyropheophorbide-a.

* * * * *